United States Patent [19]

Stevens

[11] 4,302,386

[45] Nov. 24, 1981

[54] ANTIGENIC MODIFICATION OF POLYPEPTIDES

[75] Inventor: Vernon C. Stevens, Dublin, Ohio

[73] Assignee: The Ohio State University, Columbus, Ohio

[21] Appl. No.: 112,628

[22] Filed: Jan. 16, 1980

Related U.S. Application Data

[60] Division of Ser. No. 936,876, Aug. 25, 1978, Pat. No. 4,201,770, which is a continuation-in-part of Ser. No. 622,031, Oct. 14, 1975, abandoned, which is a continuation-in-part of Ser. No. 462,955, Apr. 22, 1974, abandoned, which is a continuation-in-part of Ser. No. 406,821, Oct. 16, 1973, abandoned, which is a continuation-in-part of Ser. No. 357,892, May 7, 1973, abandoned.

[51] Int. Cl.$^3$ ...................... C07C 103/52; C07G 7/00; A61K 37/00; A61K 39/00

[52] U.S. Cl. ........................ 260/112.5 R; 260/112 R; 424/177; 424/88; 424/89

[58] Field of Search .................. 424/177; 260/112.5 R

[56] References Cited

U.S. PATENT DOCUMENTS

| | | | |
|---|---|---|---|
| 2,301,532 | 11/1942 | Fell | 424/177 |
| 2,372,066 | 3/1945 | Fell | 424/177 |
| 2,388,260 | 11/1945 | Friedhelm | 424/177 |
| 2,744,890 | 5/1956 | Wagner | 424/177 |
| 3,317,400 | 5/1967 | Reusser | 424/177 |
| 4,122,166 | 10/1978 | Tribble et al. | 424/177 |
| 4,123,519 | 10/1978 | Tribble et al. | 424/177 |
| 4,161,519 | 7/1979 | Tolwar | 424/177 |
| 4,179,337 | 12/1979 | Davis, et al. | 424/177 |
| 4,193,982 | 3/1980 | Avrameas et al. | 424/177 |
| 4,201,770 | 5/1980 | Sterens | 424/177 |

OTHER PUBLICATIONS

B. Cinader et al., J. of Experimental Medicine, vol. 125, No. 6, pp. 1057-1073 (1967).

W. E. Nixon et al., J. Lab. Clin. Med. (1971), vol. 78, No. 6, pp. 949-956.

S. J. Gross et al., Immunochemistry, vol. 5, pp. 55-65 (1968).

M. Tabachnick et al., J. of Biological Chemistry, vol. 235, 1960, pp. 1051-1054.

*Primary Examiner*—Delbert R. Phillips

*Attorney, Agent, or Firm*—Millard & Cox

[57] ABSTRACT

Modified hormones or fragments of hormones are useful in producing antibodies when administered to an animal. Said antibodies in turn cause neutralization of endogenous natural protein hormones. The modification may be accomplished by attaching various kinds of modifying groups to the hormone or fragment. Modification may, for example, be achieved by chemically coupling diazosulfanilic acid groups to the hormone or fragment. The protein hormones to which this procedure can be applied are mammalian protein reproductive hormones such as, for example, Follicle Stimulating Hormone (FSH), or Human Chorionic Gonadotropin (HGG). These modified hormone or fragment may be administered to animals for the purpose of contraception, abortion, or treatment of hormone related disease states and disorders.

35 Claims, 3 Drawing Figures

| Baboon No. | Mating 1 | | | Mating 2 | | | Mating 3 | | |
|---|---|---|---|---|---|---|---|---|---|
| | PRE-MATING TITER (ng/ml) | OVULATED | PREGNANT | PRE-MATING TITER (ng/ml) | OVULATED | PREGNANT | PRE-MATING TITER (ng/ml) | OVULATED | PREGNANT |
| 1374 | 108 | + | − | 110 | + | − | 97 | + | − |
| 1422 | 123 | + | − | 101 | + | − | 100 | + | − |
| 976 | 345 | + | − | 331 | + | − | 305 | + | − |
| 1068 | 95 | + | − | 89 | + | − | 91 | + | + |

FIG. 1

ANTIGENIC MODIFICATION OF POLYPEPTIDES

This is a Divisional of Application Ser. No. 936,876 filed Aug. 25, 1978, now U.S. Pat. No. 4,201,770, which in turn is a continuation-in-part of Ser. No. 622,031 filed Oct. 14, 1975, now abandoned, which in turn is a continuation-in-part of application Ser. No. 462,955 filed Apr. 22, 1974, now abandoned, which in turn is a continuation-in-part of application Ser. No. 406,821 filed Oct. 16, 1973, now abandoned, which in turn is a continuation-in-part of application Ser. No. 357,892, filed May 7, 1973, now abandoned.

BACKGROUND OF THE INVENTION

It is well known that antibodies are generated in humans and in other animals in response to the presence of foreign antigers. It is also known to confer immunity on an animal by administering an antibody formed elsewhere. For instance, the patents to Michaelson (U.S. Pat. No. 3,553,317), Friedheim (U.S. Pat. No. 2,388,260), Reusser (U.S. Pat. No. 3,317,400) and Peterson (U.S. Pat. No. 3,376,198) relate to production of antibodies, which when injected into an animal of a different species or into a human being cause passive immunization. In patents to Fell (U.S. Pat. Nos. 2,301,532 and 2,372,066), the patentee refers to active immunization using modified histamine in such animals as horses, cows, etc. In a paper by R. G. Edwards in the British Medical Journal, Vol. 26, pages 72 to 78, published in 1970 on "Immunology of Conception and Pregnancy", he surveys the literature regarding the possibilities of utilizing immunological methods to influence or control fertility, surveying first production of antibodies against testes or spermatozoa. Much of the literature surveyed is directed to the production of foreign antibodies which are injected into the subject (passive immunization).

Hormone antibodies have been studied for a long time and the effect of specific antisera have been recorded for many years. It is known that administration of certain antibodies during pregnancy can suppress implantation or cause fetal resorption. Several different approaches have been tried ranging from the induction of near permanent infertility in the case of agglutination of spermatozoa in the male to the disturbance of a single pregnancy by passive immunization with antibodies.

There are serious limitations to the use of passive immunization procedures for human therapy. Since the antibodies are practically produced only in non-human animals, the repeated injection of animal proteins into humans is known to produce serious reaction in many individuals.

British patent No. 1,058,828 discloses that small molecules, referred to as "serological determinant peptides," can be coupled to large protein molecules, such as cattle albumin and the resultant conjugate then may be injected into animals for antibody production. The document lists proteins from which the serologically determinant peptides may be isolated prior to being used in the process taught, the collection including viruses and bacteria whose surface component has the characteristics of a protein, toxins ad hormones having protein structure and enzymes. No specific hormone is named in the document and no utility of anti-hormone immunization is described. The patent specification references a publication entitled: "The Specificity of Serological Reactions", Dover Publications, Inc., New York, 1962, Chapter V, "Artificial Conjugated Antigens" by K. Landsteiner. This publication outlines various chemical methods and applies them passively to bind various toxic substances in the blood such as arsenic. Thyroxine data provided in the publication suggests that such methods may be applied to protein hormones without indicating the therapeutic application, the publication teaching that specific antibodies may be formed to the small molecules and these antibodies are capable of neutralizing the biological action of a large protein from which the small peptide was a part.

Recently it has been discovered that doses of certain steroids consisting of synthetic non-protein hormones ("The Pill") when administered at stated intervals usually confer protection against pregnancy for a short time (possibly a month). This medication has sometimes been found to create undesirable side effcts in creating undesirable metabolic changes and sometimes changes in the blood clotting mechanisms. Moreover, the effect of each dose is of such short duration that often it is of limited application, particularly in remote areas to persons not readily instructed on proper and continuing use.

There is need therefore of an effective safe method of creating a temporary but relatively long-time immunity against pregnancy which does not have serious side effects. There is also a need for an effective safe method of terminating a pregnancy soon after conception which does not have serious harmful side effects. Such need may be met by the neutralization of a reproductive protein which is necessary for the normal events of conception and/or gestation.

There is also a need for a means for control of various disease states or maladies caused or influenced by unusual excesses of certain polypeptides such as gastrin, angiotension II, or somatomedian. It is believed that this invention meets this need safely and effectively.

SUMMARY OF THE INVENTION

This invention is concerned (1) with the production of antigens for the purpose of active immunization, (2) with the antigens so produced, and (3) with the use of said antigens. More particularly, the invention relates to antigens consisting of natural protein reproductive hormones, non-hormonal proteins, specific fragments of such hormones and proteins and synthetically derived portions of said hormones and proteins, all modified as will be indicated more fully hereinafter. For the sake of simplicity, hereinafter in this specification and in the claims, these antigens are collectively referred to as modified polypeptides.

The invention is directed in one aspect to the use of modified polypeptides in actively immunizing an animal, particularly mammals, against the biological action of endogenous unmodified non-hormonal natural protein and/or hormone. The state of immunity arises because of the creation of antibodies which act against both the antigenic modified polypeptide and its endogenous counterpart which is neutralized (rendered biologically ineffectual) as a result of the existence of said antibodies. The immunity may take place because of the inability of the antibody to distinguish between the modified polypeptide and the naturally existing protein, but it is uncertain that this is in fact the situation. In effect, the invention provides, in one aspect, for the isoimmunization of a primate animal.

A more specific aspect of this invention relates to the modification of protein reproductive hormones by adding certain numbers of foreign moieties to each hormone molecule, or hormonal fragment. The modification must be sufficient to cause the body to create antibodies to the modified hormones which will neutralize or inhibit the biological action of the natural hormones produced by the body. Thus, the modified hormones become antigenic and cause the production of antibodies which disrupt the natural processes of conception and/or gestation. The term "protein reproductive hormones" includes those hormones essential to the normal events of the reproductive process.

According to a further aspect of this invention, a disease state which can be treated by application of the technique of the instant invention is the digestive disorder known to those skilled in the medical field as the Zollinger-Ellison Syndrome. This syndrome or disease state is generally described as a condition in which a hyper secretion of the polypeptide gastrin, which is produced in the pancreas and brings about a state of hyperacidity in the stomach which results in a chronic digestive disorder. Heretofore, the only effective treatment for this disease state was the surgical removal of a part or total removal of the subject's stomach. Although survival of such patients is usually not threatened, the medical state and life style of such individuals is severely affected by such treatment.

Treatment of such subjects with hapten coupled (produced according to the general method described herein) or otherwise chemically modified gastrin can be used to enhance the production of antibodies against the hypersecretion of gastrin and thereby alleviate or reduce the symptoms of this disease without surgical intervention. Sufficient reduction by immunological means of this substance in the system of the body would be sufficient to avoid the complicated and serious consequences of the surgical treatment currently in use. In practice, an effective amount of modified gastrin is simply injected into the patient as required to accomplish the control of the flow or presence of gastrin.

Another serious medical problem which is treatable by the application of the technique of the instant invention is that of hypertension. In general terms, the state of hypertension is the abnormal level or fluctuation of one's blood pressure. The blood pressure in an individual is controlled by many physiological processes in the body. However, one major substance effecting the regulation of such pressure is the hormonal polypeptide known as angiotension II. In certain states of high blood pressure (hypertension) it is difficult to medically control the secretion and therefore the level of angiotension II in the circulatory system. By the appropriate modification of this hormone and subsequent immunization with this altered modified proteinaceous hormone, it is possible to reduce the secretion of angiotension II in patients with chronically elevated hormone levels. The predictable and controlled reduction of this substance is beneficial to certain patients with chronic problems of hypertension. Modified angiotension II can be produced by the general protein modification technique described herein. The resultant modified angiotension II is simply injected into the patient in an amount sufficient to induce antibody response sufficient to control or regulate unmodified angiotension II to the desired degree.

A further embodiment of the present invention is the treatment of diabetes and associated micro and macro vascular diseases. Currently, the treatment of diabetes is limited to dietary and/or drug treatment to regulate blood glucose levels. Recent scientific data support the concept that growth hormone and somatomedian (both polypeptides) are intimately involved in the disease syndrome. These substances can be modified by the technique described herein and used in an effective amount to control the progress of this disease. In practice, modified growth hormone or modified somatomedian is injected into the body to develop antibodies for control of the normally secreted hormones.

Another health problem that can be treated by the use of the concepts of this invention is that of certain endocrine or hormone dependent breast tumors or cancers. Certain of these cancers have been shown to be dependent upon the abundant secretion of the hormone prolactin for their continued survival. The inhibition of the secretion of prolactin has been shown to diminish the growth rate and the actual survival of certain of these tumors. The immunization of such subjects with the hapten coupled or otherwise altered prolactin produced as described herein, would result in the systematic reduction of the level of this hormone circulating in the system and consequently, may result in the regression or remission of tumor growth. The consequence of this treatment would be far more favorable in terms of effective treatment of this disease since surgical removal of the breasts is a principal method of treatment currently available. It should be understood that this treatment should be effective for only those tumors that are dependent upon the secretion of prolactin for survival.

Investigators also have determined, for example, that certain polypeptide entities are supportive factors to and secretions of neoplastic diseases in both man and other animals. These entities have biochemically, biologically and immunologically close resemblances to hormones, particularly to Chorionic Gonadotropin (CG), as well as to Luteinizing Hormone (LH). By applying the isoimmunization techniques of the invention, the function of such polypeptides or endogenous counterparts can be neutralized to carry out regulation of the malignancy. For example, tumors in both male and female primates may be treated by isoimmunization procedures developing antibodies to Chorionic Gonadotropin or Luteinizing Hormone or the noted entity analogous thereto. Further, neoplasms in primate females may be regulated by isoimmunization procedures developing antibodies to endogenous Follicle Stimulating Hormone (FSH). This hormone, when associated with a tumor state, tends to aggravate the tumorous condition.

The immunochemical control asserted, as noted, neutralizes the naturally occuring hormone or the above-described entity biologically analogous thereto. As a consequence, the hormone or entity will not be available as would normally be the case, for example, the stimulation of some action of a target tissue. Conversely, the neutralization of the biological activity of the hormone or analogous entity may serve to take away an inhibitory action which it otherwise might assert.

There are certain other disease states that may be treatable by the use of altered or modified hormonal or non-hormonal proteins as antigens. The disease states and the associated substances that may be used as modified antigens for immunological treatment of these diseases will be listed as follows:

(1) modified parathyroid hormone for the treatment of kidney stones, (2) modified insulin and/or glucagon for the treatment of hyperinsulinoma,
(3) modified thyroid stimulating hormone (TSH) for the treatment of hyperthyroidism, and
(4) modified secretin for the treatment of irritable bowel syndrome.

Another group of polypeptides which can be altered by the procedures described herein and used in the field of human fertility control are specific non-hormonal protein antigens isolated from placental tissue. There is direct evidence that inhibition of substances that are specific to the placental tissue and do not have similar antigenic properties with other antigens from organs in other parts of the body, can result in the disruption of pregnancies by passive immunization. Such specific placental substances when modified to form modified polypeptides by the procedures described herein can be injected into the body of an animal of the same species as an effective fertility control means with the mechanism being active immunization similar to that described for the antigenic modification of hormones. The particular advantages of these substances in that placental antigens are foreign to the non-pregnant female human subject and therefore are unlikely to cause any cross-reaction or disruption of normal body function in the non-pregnant female.

While the invention is useful for the human species it will be appreciated that it is also useful in connection with other animals. Similarly, while the reference herein with respect to fertility control is primarily directed to females, such described techniques may be applicable to males, i.e. FSH, its beta subunit and fragments thereof. Such immunization represents an effective fertility control procedure, providing no physiological consequences are encountered which may be found to react adversely to the performance of other body constituents.

Whether the concerned hormone, non-hormonal protein or specific fragment thereof which is modified is naturally occurring or is a synthetic product is clearly immaterial. A synthetic protein molecule will perform the same function as the naturally occurring one, inasmuch as the body will react in an equivalent antigenic manner.

It has accordingly been discovered by virtue of this invention that it is possible to interfere with or treat various disease states or medical problems which are caused or influenced by certain polypeptides by active immunization of a male or female animal by the production and use of antigens formed by administration of modified polypeptides. The modification of the polypeptides forms antigens which are then administered into an animal in which immunization is to be developed. Said modification is accomplished by attaching to a polypeptide one or more foreign reactive (modifying) groups and/or by attaching two or more polypeptides to a foreign reactive group (i.e., a carrier) or both of the above, so that the body of the animal, recognizing the modified polypeptide as a foreign object, produces antibodies which neutralize not only the modified protein but also the natural protein which is responsible for the disease or medical problem being regulated. In order to produce an effective quanta of antibodies to the antigen or targeted functional polypeptide, it may be advantageous to administer the modified polypeptide together with an immunological adjuvant. The term "adjuvant" is commonly referred to by those engaged in the field at hand as being a substance which will elevate the total immune response of an animal or person to any immunization thereof, i.e. the adjuvant is a nonspecific immuno-stimulator.

BRIEF DESCRIPTION OF THE DRAWINGS

FIG. 1 is a chart describing the results of mating four baboons three times following the administration thereto of a fertility controlling antigen according to the invention;

GENERAL DESCRIPTION

Figure 2:
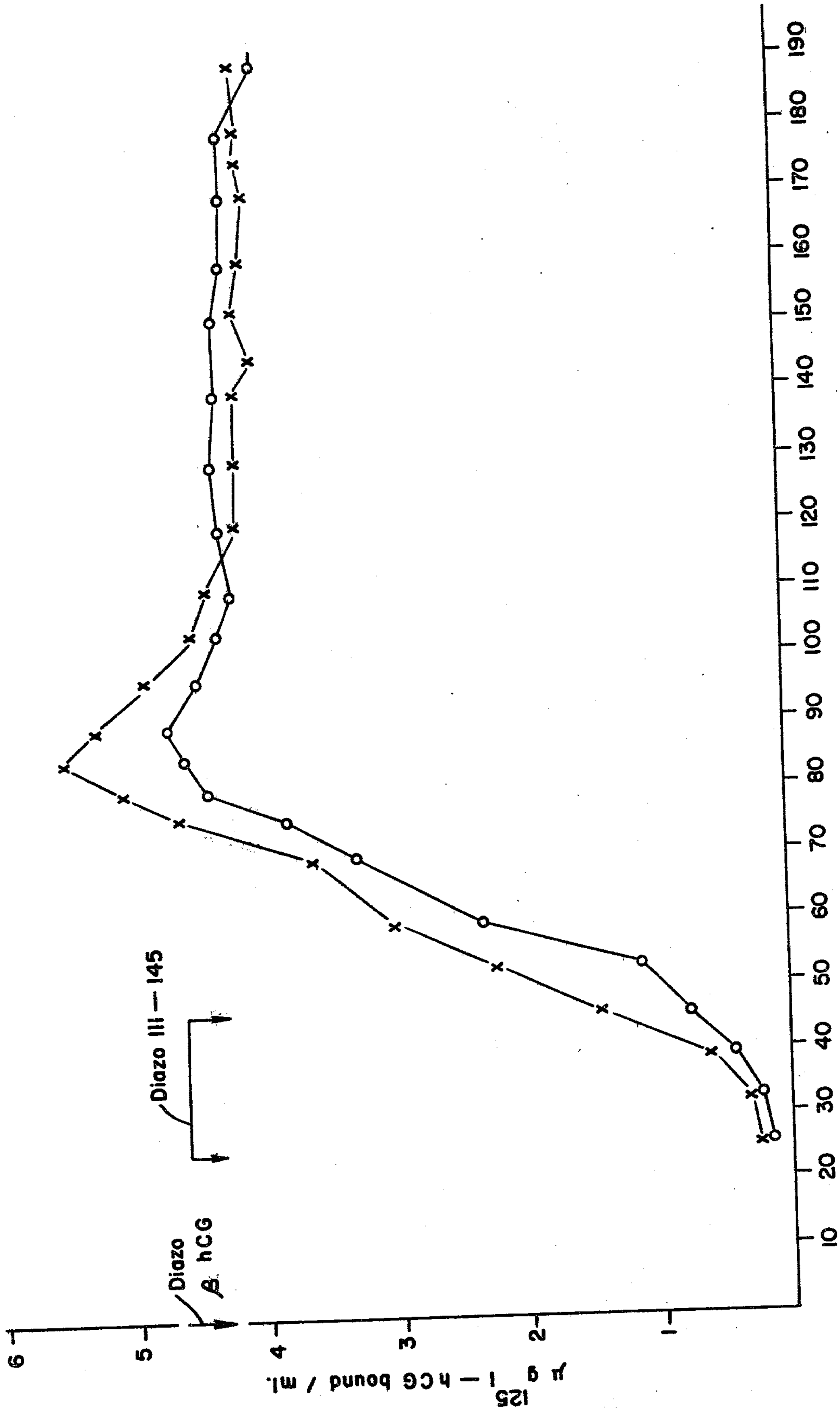
FIG. 2 shows two plots illustrating the antifertility antibody levels maintained within two baboons following the administration of antigens thereto formulated in accordance with the invention.

In an effort to better define the modified polypeptides with which this invention is concerned, it is first considered appropriate to set out more precisely than hereinabove, examples of the natural hormones and natural non-hormonal proteins modified according to this invention. They include Follicle Stimulating Hormone (FSH), Luteinizing Hormone (LH), Chorionic Gonadotropin (CG), e.g. Human Chorionic Gonadotropin (HCG), Placental Lactogen, e.g. Human Placental Lactogen (HPL) Prolactin, e.g. Human Prolactin (all of which are proteinaceous reproductive hormones), gastrin, angiotension II, growth hormone, somatomedian, parathyroid hormone, insulin, glucagon, thyroid stimulating hormone (TSH), secretin, and other polypeptides which could adversely affect body function.

The hormone Chorionic Gonadotropin (CG) has been the subject of extensive investigation, it being demonstrated in 1927 that the blood and urine of pregnant women contained a gonad-stimulating substance which, when injected into laboratory animals, produced marked gonadal growth. Later, investigators demonstrated with certainty that the Placental Chorionic villi, as opposed to the pituitary, were the source of this hormone. Thus, the name Chorionic Gonadotropin or, in the case of humans, Human Chorionic Gonadotropin (HCG) was given to this hormone of pregnancy. During the more recent past, a broadened variety of studies have been conducted to describe levels of HCG in normal and abnormal physiological states, indicating its role in maintaining pregnancy. The studies have shown the hormone's ability to induce ovulation and to stimulate corpus luteum function and evidence has been evoked for showing its ability to suppress lymphocyte action. The immunological properties of the HCG molecule also have been studied widely. Cross-reaction of antibodies to HCG with human pituitary Luteinizing Hormone (LH), and vice-versa, have been extensively documented, see for example:

Paul, W. E. & Ross, F. T. (1964) Immunological Cross Reaction Between HCG and Human Pituitary Gonadotropin. *Endrocrinology,* Vol. 75, pp. 352-358.

Flux, D. X. & Li C. H. (1965) Immunological Cross Reaction Among Gonadotropins. *Acta Endocrinologica,* Vol. 48, pp. 61-72.

Bogshawe, K. D.; Orr, A. H. & Godden J. (1968) Cross-Reaction in Radio-Immunoassay between HCG and Plasma from Various Species. *Journal of Endocrinology,* Vol. 42, pp. 513-518.

Franchimont, P. (1970) Study on the Cross-Reaction between HCG and Pituitary LH. *European Journal of Clinical Investigation,* Vol. 1, pp. 65-68.

Dorner, M.; Brossmer, R.; Hilgenfeldt, U. & Trude, E. (1972). Immunological reactions of Antibodies to HCG with HCG and its chemical derivatives. *In Structure-Activity Relationships of Proteins and Polypeptide Hormones* (ed. M. Margoulies & F. C. Greenwood), pp. 539, 541 Amsterdam: Exerpta Medica Foundation.

Further, these cross-reactions have been used to perform immunoassays for both CG and LM hormones. See:

Midgley, A. R. Jr. (1966) Radioimmunoassay: a method for HCG and LH. *Endocrinology,* Vol. 79, pp. 10-16.

Crosignani, P. G., Polvani, F. & Saracci R. (1969) Characteristics of a radioimmunoassay for HCE-LH. In *Protein and Polypeptide Hormones* (ed. M. Margoulies) pp. 409, 411 Amsterdam: Excerpta Medica Foundation.

Isojima, S; Nake, O.; Kojama, K. & Adachi, H. (1970). Rapid radioimmunoassay of human L.H. using polymerized anti-human HCG as immunoadsorbent. *Journal of Clinical Endocrinology and Metabolism,* Vol. 31, pp. 693-699.

constituent, LH, may be eliminated. Synthetic equivalents of the fragments offer enhanced practicality both from the standpoint of production costs and necessary maintenance of purity.

As is indicated in the above discussion, when considered in isolation with respect to conception and pregnancy, CG only is present in female primates when they are in a post conception state. However, as discussed above and later herein, an entity at least analogous thereto (having similar immunological properties to HCG) is seen to be present in conjunction with malignancies.

Subunits and fragments of the proteinaceous reproductive hormones include the beta subunit of natural Follicle Stimulating Hormone, the beta subunit of natural Human Chorionic Gonadotropin, fragments including, inter alia, a 20-30 or 30-39 amino acid peptide consisting of the C-terminal residues of natural Human Chorionic Gonadotropin beta subunit, as well as specific unique fragments of natural Human Prolactin and natural Human Placental Lactogen, which may bear little resemblance to analogous portions of other protein hormones. Further with respect to the type of novel chemical entities with which this invention is concerned, one may note for instance the chemical configuration of the beta subunit of HCG. That structure is as follows:

Structure (I)

10 (Arg) * (Asn)
Ser—Lys—Glu—Pro—Leu—Arg—Pro—Arg—Cys—Arg—Pro—Ile—Asn—Ala—Thr—
20 (Lys) * (Asn)
Leu—Ala—Val—Glu—Lys—Glu—Gly—Cys—Pro—Val—Cys—Ile—Thr—Val—Asn—
40 (Thr)
Thr—Thr—Ile—Cys—Ala—Gly—Try—Cys—Pro—Thr—Met—Thr—Arg—Val—Leu—
50 (Pro) 60 (Arg)
Gln—Gly—Val—Leu—Pro—Ala—Leu—Pro—Gln—Val—Val—Cys—Asn—Try—Arg—
70 (Pro)
Asp—Val—Arg—Phe—Glu—Ser—Ile—Arg—Leu—Pro—Gly—Cys—Pro—Arg—Gly—
80 (Val) 90 (Cys)
Val—Asn—Pro—Val—Val—Ser—Tyr—Ala—Val—Ala—Leu—Ser—Cys—Gln—Cys—
100 (Cys)
Ala—Leu—Cys—Arg—Arg—Ser—Thr—Thr—Asp—Cys—Gly—Gly—Pro—Lys—Asp—
110 (Cys) 120 (Ser)
His—Pro—Leu—Thr—Cys—Asp—Asp—Pro—Arg—Phe—Gln—Asp—Ser—Ser—Ser—
* (Ser) * (Ser) 130 (Ser) * (Ser)
Ser—Lys—Ala—Pro—Pro—Pro—Ser—Leu—Pro—Ser—Pro—Ser—Arg—Leu—Pro—
* (Ser) 140 (Thr)
Gly—Pro—Ser—Asp—Thr—Pro—Ile—Leu—Pro—Gln

*indicates site location of carbohydrate moieties on natural polypeptide.

In addition to providing for the modification of the entire hormone or selected polypeptide, the invention further provides for the utilization of modified subunits, for example the beta subunit of Chorinonic Gonadotropin. Of particular interest, such subunits may be fragmented into smaller components herein termed "fragments". The latter can be produced synthetically to exhibit an amino acid sequence sufficiently in analogous correspondence to a predetermined portion of the parent subunit. Such fragments generally are conjugated with a larger molecule or component foreign to the body, which may be termed a "carrier", in order to effectively evoke or raise a sufficient quanta of antibodies. The use of the fragments, as thus conjugated, advantageously provides a high degree of specificity of antigenic reaction to the targeted hormone or its biochemical equivalent, i.e. the antibodies will not react with other body constituents. Of particular interest, the above-discussed cross reaction of HCG and LH can be avoided by utilization of fragments of the respective hormone due to the desirable specificity of response thereto. Thus, when interested in obtaining an immunological reaction against the hormone, HCG, the undesirable immune reaction to the naturally occuring body For specificity of antibody action it is necessary that distinctive peptides be isolated or prepared that contain molecular structures completely or substantially completely different from the other hormones. The beta-subunit of HCG possesses a specific chain or chains of amino acid moieties which differ either completely or essentially from the polypeptide chain of Human Luteinizing Hormone. These chains or fragments, when conjugated with a carrier, represent an additional aspect of this invention. Accordingly, the polypeptide structures (II) and (III) [C-terminal portion of structure (I)]

Asp-Asp-Pro-Arg-Phe-Gln-Asp-Ser-Ser-Ser-Ser*-
Lys-Ala-Pro-Pro-Pro-Ser*-Leu-Pro-Ser-Pro-Ser*-
Arg-Leu-Pro-Gly-Pro-Ser*-Asp-Thr-Pro-Ile-Leu-
Pro-Gln

Structure (II)

Gln-Asp-Ser-Ser-Ser-Ser*-Lys-Ala-Pro-Pro-Pro-Ser*-
Leu-Pro-Ser-Pro-Ser*-Arg-Leu-Pro-Gly-Pro-Ser*-
Asp-Thr-Pro-Ile-Leu-Pro-Gln

Structure (III)

whether obtained by purely synthetic methods or by enzymatic degradation from the natural or parent polypeptide, [Carlson et al., J. Biological Chemistry, 284 (19), p. 6810, (1973)] when modified according to this invention, similarly provide materials with antigenic properties sufficient to provide the desired immunological response. It will be understood, for example, that additon of a polytyrosine chain or a protein macromolecule (carrier) may assist in rendering structure (II) antigenic so that the resulting administration of modified structure (II) will provide the desired immunological action against natural HCG.

The beta subunit set forth at structure (I) is seen to represent a chemical sequence of 145 amino acid components. This structure has a high degree of structural homology with the corresponding subunit of Luteinizing Hormone (LH) to the extent of the initial 110 amino acid components. As incicated above, it may be found desirable, therefore, to evoke a high specificity to the Chorionic Gonadotropin hormone or an analogous entity through the use of fragments analogous to the C-terminal, 111–145 amino acid sequence of the subunit. Structure (II) above may be observed to represent just that sequence. Structure (III) is slightly shorter, representing the 116–145 amino acid positions within the subunit sequence.

Further polypeptide chains useful in promoting antibody buildup against natural HCG include the following structures labeled Structures (IV) through (XIV). When modified according to this disclosure, such as by coupling to Ficoll 70* or other modifier-carriers such as protein macromolecules described herein, these polypeptides provide immunogenic activity with which this invention is concerned. All of these polypeptides are considered fragments of HCG by virtue of their substantial resemblance to the chemical configuration of the natural hormone and the immunological response provided by them when modified as indicated herein.

Cys-Pro-Pro-Pro-Pro-Pro-Pro-Ser-Asp-Thr-Pro-Ile-Leu-Pro-Gln

Structure (IV)

Asp-Asp-Pro-Arg-Phe-Gln-Asp-Ser-Pro-Pro-Pro-Pro-Pro-Pro-Cys

Structure (V)

Phe-Gln-Asp-Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln

Structure (VI)

Asp-Asp-Pro-Arg-Phe-Gln-Asp-Ser-Ser-Ser-Ser-Lys-Als-Pro-Pro-Pro-Ser-Leu-Pro-Ser

Structure (VII)

Asp-Asp-Pro-Arg-Phe-Gln-Asp-Ser-Pro-Pro-Pro-Cys-Pro-Pro-Pro-Ser-Asp-Thr-Pro-Ile-Leu-Pro-Gln

Structure (VIII)

Asp-Asp-Pro-Arg-Phe-Gln-Asp-Ser-Pro-Pro-Pro-Pro-Pro-Pro-Cys-Pro-Pro-Pro-Pro-Pro-Pro-Ser-Asp-Thr-Pro-Ile-Leu-Pro-Gln

Structure (VIIIa)

*Pharmacia Fine Chemicals, Pharmacia Laboratories, Inc., 800 Centennial Ave., Piscataway, N.J. 08854

A synthetic copolymer of sucrose and epicholorohydrin having an average molecular weight of 70,000±10,000, good solubility in water, Stokes radius about 5.1, stable in alkaline and neutral media.

Asp-His-Pro-Leu-Thr-Aba-Asp-Asp-Pro-Arg-Phe-Gln-Asp-Ser-Ser-Ser-Ser-Lys-Als-Pro-Pro-Pro-Ser-Leu-Pro-Ser-Pro-Ser-Arg-Leu-Pro-Gly-Pro-Ser-Asp-Thr-Pro-Ile-Leu-Pro-Gln-Pro-Pro-Pro-Pro-Pro-Pro-Cys

Structure (IX)

Asp-Asp-Pro-Arg-Phe-Gln-Asp-Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln-Pro-Pro-Pro-Pro-Pro-Pro-Cys

Structure (X)

Asp-Asp-Pro-Arg-Phe-Gln-Asp-Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln-Cys

Structure (XI)

Structure (IV) will be recognized as incorporating a Cys component at the amino or N terminal which is associated with a Proline spacer sequence. These spacers serve to position the sequence which follows physically distant from the carrier-modifier. The latter sequence may be observed to represent the 138th to 145th amino acid component sequence of the subunit Structure (I). Structure (V) on the other hand, represents an initial sequence corresponding with the 111th to 118th components of the subunit Structure (I) followed by a sequence of six Proline spacer components and a carboxyl terminal, present as Cysteine. The rationale in providing such a structure is to eliminate the provision of sites which may remain antigenically neutral in performance. Structures (IV) and (V) represent relatively shorter amino acid sequences to the extent that each serves to develop one determinant site. Consequently, as alluded to in more detail hereinafter, they are utilized in conjunction with a mixed immunization technique wherein a necessary two distinct determinants are provided by the simultaneous administration of two such fragments, each conjugated to a corresponding, separate carrier macromolecule. Structure (VI) represents the 115th through 145th component sequence of Structure (I). Structure (VII) represents a portion of Structure (I), however, essentially, a sequence of the 111th to 130th components thereof is formed.

Structure (VIII) incorporates two sequences, one which may be recognized in Structure (V) and the other in Structure (IV). These two sequences are separated by two spacer sequences of Proline components and one is joined with an intermediately disposed Cysteine component which serves a conjugation function as described later herein. With the arrangement, two distinct determinant sites are developed in physically spaced relationship to avoid the development of an unwanted artificial determinant possibly otherwise evolved in the vicinity of their mutual coupling. Structure (VIIIa) represents Structure (VIII) with additional Pro spacer residues to provide a widened spacing of determinant sites.

Structure (IX) mimics sequences from Structure (I) with the addition of a Proline Spacer Sequence, a Cysteine Component at the C-terminal, and an Aba substituted for Cys at the 110 position. The Aba designation is intended herein to mean alpha-aminobutyric acid of Cysteine. Structure (X) will be recognized as a combination of Structure (II) with a six residue Proline spacer sequence and a Cysteine component at the C-terminal. Similarly, Structure (XI) combines Structure (II) with a Cysteine component at the C-terminal without a Proline spacer sequence.

Thr-Cys-Asp-Asp-Pro-Arg-Phe-Gln-Asp-Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln

Structure (XII)

Asp-His-Pro-Leu-Thr-Aba-Asp-Asp-Pro-Arg-Phe-Gln-Asp-Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln-Cys

Structure (XIII)

Cys-Pro-Pro-Pro-Pro-Pro-Pro-Asp-Asp-Pro-Arg-Phe-Gln-Asp-Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln

Structure (XIV)

Structure (XII) will be recognized as having the sequence of Structure (II) with the addition of Thr-Cys components at its N terminal. Structure (XIII) is similar to Structure (IX) but does not contain the spacer conjugate. Structure (XIV) will be recognized as being similar to Structure (II) with the addition of spacer components at the N terminal and a Cys component for conjugation purposes.

Particularly where the larger whole hormone or subunit type molecular structures are concerned, the number of foreign reactive groups which are to be attached to the polypeptide and the number of polypeptides to be attached to a foreign reaction group depends on the specific problem being treated. Basically, what is required is that the concerned polypeptide be modified to a degree sufficient to cause it to be antigenic when injected in the body of the host. If too little modification is effected, the body may not recognize the modified polypeptide as a foreign body and would not create antibodies against it. If the number of foreign molecules added to the polypeptide is too great, the body will create antibodies against the intruder antigen, but the antibodies will be specific to the injected antigen and will not neutralize the action of the concerned natural endogenous hormone or non-hormonal protein, i.e. they will be specific to the modifier.

In general, again considering the larger molecule subunit or whole hormone, it has been found that about 1–40 modifying groups per molecule of polypeptide will be useful in modifying the polypeptide adequately so as to obtain the desired immunological effect of this invention. As will be appreciated by one skilled in the art, this ratio of modifying groups per polypeptide will vary depending upon whether an entire hormone is utilized for modification or whether for instance a relatively small synthetic fragment of said hormone is to be modified. Generally for the larger molecules, it is preferred that 2–40 modifying groups per molecule of polypeptide be used according to this invention. In the instance where the polypeptide is the beta-subunit of HCG it is particularly preferred that about 5–30 and more preferably 10–26 modifying groups per molecule of polypeptide be used. The important consideration with respect to each modified polypeptide is that the degree of modification be adequate to induce generation by the body of antibodies adequate to neutralize some of the natural hormone or non-hormonal protein against which neutralization is desired, and this will vary with each polypeptide involved, and the degree of correction or change desired for the body function involved.

Modification of the polypeptide is accomplished by attaching various kinds of modifying groups to proteinaceous hormone, non-hormonal proteins, subunits or specific fragments thereof according to methods known in the art.

As is apparent, Structures (II)–(XIV) are relatively smaller fragments, usually produced synthetically. To render them capable of eliciting antibody production, it becomes necessary to conjugate them with larger carrier-modifier molecules. Generally about 5–30 peptide fragments will be coupled with one carrier molecule. The body will, in effect, recognize these foreign carriers as well as the sequences represented by the fragments and form antibodies both to the carrier and to the sequences of the coupled fragments. Note that the carrier-modifiers are foreign to the body and thus antibodies to them will not be harmful to any normal body constituents. In the latter regard, it may be found preferable to utilize a carrier which, through the development of antibodies specific to it, will be found beneficial to the recipient.

As indicated earlier herein, it also is preferred that the modification constitute two or more immunological determinants represented on the native hormone as polypeptide structures to which it is desired to evoke an antibody response. The effect is one of heterogeneity of antibody development. Thus, several fragment structures have been described above having at least two distinct amino acid sequences represented in the HCG beta subunit [Structure (I)]. These sequences may be so spaced as to derive the determinants in mutual isolation, while the spaced sequence fragment is conjugated with a larger, macromolecular carrier. Alternately, the noted mixed immunization arrangement may be utilized wherein a first fragment developing one determinant is conjugated with a first carrier molecule and is administered in combination with a second, distinct fragment which is conjugated with a second carrier molecule, the latter of which may be the same as or different in structure from the first carrier. Thus, each macromolecular carrier must be conjugated with hormone fragments such that each fragment represents two or more immunological determinants. These two necessary determinants can be evolved by mixing, for example, separate conjugate structures, for example Structures (IV) and (V) each of which, through forming antibodies separately to the distinct determinants, will provide a population of antibodies reacting with two separate determinants on the natural endogenous hormone.

Inasmuch as the noted fragments are relatively small as compared, for instance, to a whole hormone or subunit thereof, a criterion of size is imposed upon the selection of a carrier. The carrier size must be adequate for the body immune system to recognize its foreign nature and raise antibodies to it. Additionally, carrier selection preferably is predicated upon the noted antibody heterogeneity requirement, i.e. the carrier must itself evoke a heterogeneous immune response in addition to the fragments. For example, improved response may be recognized where the carrier is varied in structure, e.g. incorporating branching chains to enhance the recognition of both the carrier and the attached polypeptide as being of a foreign nature.

As one example of whole hormone modification, modified diazo groups derived from sulfanilic acid may be attached to the subject polypeptides, see the Cinader et al and Phillips et al references cited subsequently for instruction on how this "attachment" is accomplished, and to the extent necessary for an understanding of this invention, such is incorporated herein by reference.

Additional modifying groups for modifying whole hormones or their subunits are those groups obtained by reaction of the polypeptides with dinitrophenol, trinitrophenol, and S-acetomercaptosuccinic anhydride, while, suited for utilization as a carrier-modifier in conjunction with fragments, are polytyrosine in either straight or branched chains, polyalanines in straight or branched chains, biodegradable polydextran, e.g. polymerized sugars such as sucrose copolymerized with epichlorohydrin, e.g. Ficoll 70 and Ficoll 400* or a polyglucose such as Dextran T 70**, serum proteins such as homologous serum albumin, hemocyanin from Keyhole limpet, a marine gastropodmollusk, viruses such as influenza virus (type A, B, or C) or poliomyelitis virus, live or killed, Types 1, 2 and 3 of tetanus toxoid, diphtheria toxoid, cholera organisms or somewhat less preferably, natural proteins such as thyroglobulin, and the like. Generally, synthetic modifiers are preferred over the natural modifiers. However, carrier-modifiers found particularly suitable for conjugation with the above-discussed fragment structures are Flagellin, tetanus toxoid and an influenza subunit, for example, the preparation of which is described by Bachmeyer, Schmidt and Liehi, "Preparation and Properties of a Novel Influenza Subunit Vaccine", Post-Graduate Medical Journal (June, 1976) 52:360-367. This influenza subunit was developed as a vaccine which incorporates essentially only the two viral proteins, Haemagglutinin and Neuraminidase. Containing substantially only these two essential immunogens, the subunit represents a preparation which does not contain other protein and lipid antigens which may be found to cause undesired side reactions. A secondary benefit may be realized through the utilization for example, of the influenza subunit,

*Pharmacia Fine Chemicals, Pharmacia Laboratories, Inc. 800 Centennial Ave., Piscataway, N.J. 08854.

A synthetic copolymer of sucrose and epichlorohydrin having an average molecular weight of 400,000±100,000 intrinsic viscosity of 0.17 dl/g. specific rotation $[\alpha]_D^{20}$ of +56.5°

**Synthesized microbiologically by the action of leuconostoc mesenteroides (a strain in NRRL B-512) on sucrose. Glucan containing alpha-1, 6-glucosidic bonds. Average molecular weight approximately 70,000.

poliomyelitis virus, tetanus toxoid, diphtheria toxoid, cholera antigens or the like as a modifier-carrier, inasmuch as beneficial antibodies will be raised to that modifier-carrier as well as to the hormonal fragment conjugated thereto.

Flagellin is a protein described as forming the wall of the main spiral filament of the flagellum. Bacterial flagella, in turn, have been known as the active organelles of cell locomotion, individual flagella (flagellum) occurring in suspension as individual spirals which, upon drying, collapse into filaments which describe a sine wave with a wave length of 2-3 microns and an amplitude of 0.25-0.60 microns. Generally, the flagellum consists of three morphologically distinct parts: a basal structure that is closely associated with the cytoplasmic membrane and cell wall, a hook and the noted main spiral filament.

Purified flagellum is readily obtained by solubilization of flagellar filaments below a pH value of about four, and subsequent removal of the insoluble material by centrifugation or filtration. As a group of related proteins, flagellins from different bacterial species have been predicted to have similar amino-acid compositions. However, the amino acid composition of each flagellin species is unique. Essentially all flagellins are described as containing no or only a few residues of cysteine, tryptophan, tyrosine, proline and histidine. Thus, when conjugated with fragments in accordance with the invention, a thiolactonization procedure or the like is carried out as described later herein.

The molecular weights of various flagellin have been calculated, in all cases the values thereof of the monomeric subunits falling in the range of 30,000 to 50,000. From an immunological standpoint, a flagellin molecule is highly immunogenic. For a further and more detailed discourse describing bacterial flagella and flagellin, reference is made to "Advances in Microbial Physiology" 6:219 1971, "Bacterial Flagella" by R. W. Smith and Henry Coffler, which publication is incorporated herein by reference.

Tetanus toxoids have been the subject of study and production for many years. The toxoid generally is evolved from a formalinization of tetanus toxin, the latter being a protein synthesized by Clostridium tetani. Immunization currently is carried out utilizing soluble and absorbed tetanus toxoids and suggestions have been made concerning the utilization of fluid tetanus toxoid in complex with antitoxin. Publications describing the toxin and toxoid are numerous, reference being made to the following:

1. Immunochemistry of Tetanus Toxin, Bizzini, et al, Journal of Biochemistry, Vol. 39, pp. 171-181 (1973).
2. Early and Enhanced Antitoxin Responses Elicited with Complexes of Tetanus, Toxoid and Specific Mouse and Human Antibodies, Stoner et al, Journal of Infectious Diseases, Vol. 131, No. 3, pp. 230-238 (1975).
3. Differences in Primary and Secondary Immunizability of Inbred Mice Strains, Ipsen, Journal of Immunology, Vol. 83, pp. 448-457 (1959).
4. Antigenic Thresholds of Antitoxin Responses Elicited in Irradiated Mice with Complexes of Tetanus Toxin and Specific Antibody, Hess et al, Radiation Research, Vol. 25, pp. 655-667 (1965).
5. Early and Enhanced Germinal Center Formation and Antibody Responses in Mice After Primary Stimulation with Antigenisologous Antibody Complexes as Compared with Antigen Alone, Laissue et al, Journal of Immunology, Vol. 107, pp.822-825, (1971).
6. Distinctive Medullary and Germinal Center Proliferative Patterns in Mouse Lymph Nodes after Regional Primary and Secondary Stimulation with Tetanus Toxoid, Buerki et al, Journal of Immunology, Vol. 112, No. 6, pp. 1961-1970 (1974).

Modification by removal of moieties is also contemplated by this invention. Thus, for example, where certain of the natural proteins have carbohydrate moieties, these carbohydrate moieties may be removed according to methods known in the art by, for instance, N-acetyl neuriminidase of N-acetyl glucosidase, materials useful for removal of specific carbohydrate moieties.

These various means for modification are, as indicated above, known to persons skilled in the art. Certain of these means may be found in the following list of literature references, whereas various others of them may be found elsewhere in the literature by art-skilled persons:

(1) Klotz et al., Arch. of Biochem. and Biophys., 96, pp. 605-612, (1966).
(2) Khorana, Chem. Rev. S3: 145, (1953).
(3) Sela et al., Biochem. J., 85, p. 223, (1962)-
(4) Eisen et al., J. Am. Chem. Soc. 75, 4583, (1953).
(5) Centeno et al., Fed. Proc. (ABSTR) 25; 729, (1966).
(6) Sokolowsky et al. J. Am. Chem., Soc. 86: 1212, (1964)-
(7) Tabachnick et al., J. Biol. Chem. 234, No. 7, p. 1726, (1959).
(8) Crampton et al., Proc. Soc. Exper. Biol. & Med. 80: 448, (1952).
(9) Goodfriend et al., Science 144, p. 1344 (1964).
(10) Sela et al., J. Am. Chem. Soc., 78, p. 746, (1955).
(11) Cinader et al., Brit. of Exp. Pathol. 36, p. 515, (1955).
(12) Phillips et al, J. of Biol. Chem. 240 (2), pp. 699-704, (1965).
(13) Bahl, J. of Biol. Chem., 244, p. 575, (1969).

Methods for preparing the modified polypeptides of this invention also include the following.

In one preferred modification approach, the polypeptide fraction, for example, Structure (XII), is activated first following which is conjugated with a carrier, for example the influenza subunit described above, tetanus texoid or Flagellin. An activating reagent may be utilized which exhibits differing functionality at its ends and by choice of reaction conditions, these end components can be made to react selectively. For example, the following activator A and B, having a maleiimido group and a substituted acid group, may be provided:

"maleiimido" group

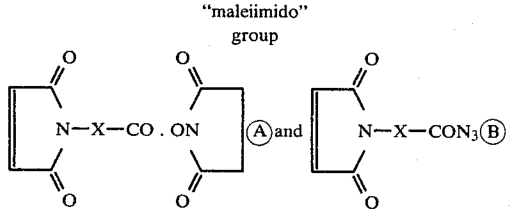

where X is a non-reacting group made up of a substituted, or unsubstituted phenyl or $C_1$–$C_{10}$ alkalene moiety, or a combination thereof. In this regard, the moiety substituted on the phenyl should be non-interfering as is the remainder of the "X" grouping. X may, inter alia, be selected from the following:

X = $-(CH_2)_5$, or

X = 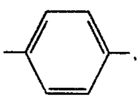, or

-continued

X = 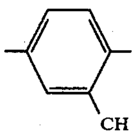

The maleiimido grouping of the above reagents will react with sulfhydryl (SH) groups in the polypeptide fragments under conditions whereby the opposite end (active ester end) of the reagent does not react with the amino groups present in the fragment sequences. Thus, for example, polypeptide fragments such as Structure (XII), containing a Cys amino acid and hence, an SH group react as follows:

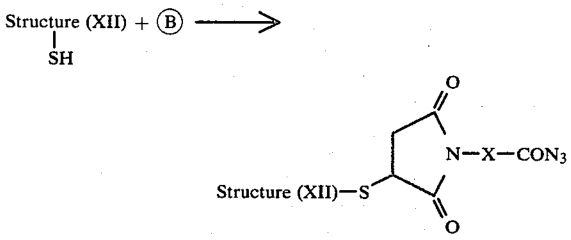

Following the above, upon adjusting the pH to a slightly alkaline condition, e.g. 8, and adding the carrier protein accomplishes the following conjugation:

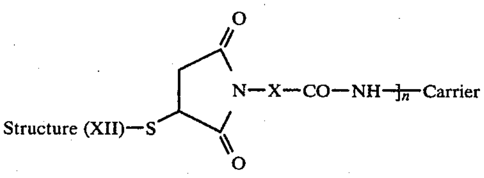

Alternately, a carrier protein such as the above-noted Flagellin which does not contain SH groups, but does contain $NH_2$ groups, may first be treated with activator A or B at pH 7 or lower at the active ester end, giving:

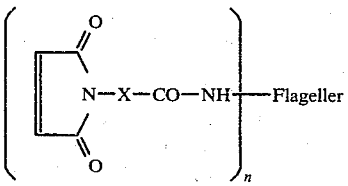

Following the above, the activated carrier is reacted with a polypeptide fragment containing an SH group to derive a product similar to that discussed immediately above.

Should the polypeptide fragment not contain an SH group, e.g. Structures (II), (III), (VI) and (VII), such structures can be modified first to introduce such a grouping by standard methods such as "thiolactonization", following which they are conjugated utilizing the above-discussed selective bi-functional reagents. For a more detailed description of these reagents, reference is made to the following publications:

O. Keller and J. Rudinger, Helv. Chim. Acta 58, 531-541 (1975).

W. Trommer, H. Kolkenbrock & G. Pfleiderer, Hoppe-Seyler's Z. Physiol. Chem., 356, 1455-1458 (1975).

Further description of preferred embodiments of the above-described utilization of bi-functional reagents is provided hereinbelow at Examples XXVII and XXVIII.

As an alternate approach to the utilization of the maleiimido group reagents discussed above, an alkylation step may be used to cause conjugation. Conditions can be chosen such that in the presence of amino groups, essentially only SH groups will be alkylated. With this approach, a generalization of the reactions carried out may be expressed as follows:

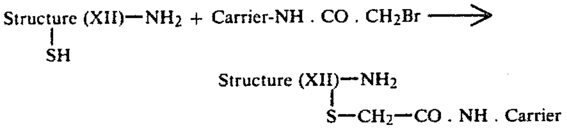

With this approach, the larger molecule carrier, e.g. Flagellin, tetanus toxoid or the influenza subunit described herein is first modified by reaction of a fraction of its amino groups with an active ester of chloro, dichloro, bromo or iodo acetic acid, such as:

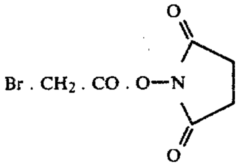

and this modified carrier is then reacted with the sulfhydryl group in a polypeptide fraction, or a polypeptide fraction which has been modified to contain the SH group (e.g. thiolactonization) if it does not already have such a group. Such modification is described in Example XXV below. The present approach produces a thio ether linkage by alkylation of a free thiol (sulfhydryl group).

With the instant procedure, the roles of the fragment and carrier may be reversed, the fragment being modified to contain the halomethyl alkylating group which would then react with sulfhydryl groups in the carrier, or a carrier suitably modified to exhibit a sulfhydryl group. More description of this selective alkylation of sulfhydryl groups is provided in conjunction with Example XXX below.

It may be seen from an observation of the formulae of Structures (IV), (V), (IX), (X), (XI), (XII), (XIII) and (XIV) that a Cys amino acid, which in a reduced state provides an SH reactive group, is located at either the C terminal or N terminal of the peptide structure. This location permits the peptide to be chemically linked to carrier molecules at either terminus. And some Structures (XIV), (X), (IX), (X), (IV) have a six-proline spacer chain $(Pro)_6$ between the Cys residue and the remainder of the peptide sequence. This latter arrangement provides a chemical spacer between the coupled carrier and the sequences representing a fragment of the natural hormone. A six-proline spacer can be added as a side chain spacer, for example at position 122 (Lys) in Structure (II), by initially adding an SH group (thiolactonization) to the free or unblocked epsilon amino group on this (Lys) residue, as set out in Example XXIX below. Then, utilizing the activator A,B above in which the component "X" is a chain of six proline amino acid, conjugation can be carried out. In the latter case, a spacer is provided between the carrier and peptide linked at an intermediate site, for example at position 122 in Structure (II). In the former case, only the space represented by conjugating reagent links the carrier and peptide.

Modifying groups, such as hemocyanin from Keyhole limpet, containing free amino groups, are prepared in buffer solution such as phosphate buffer, is sodium chloride solution at a pH of 6-8. To this solution, tolylene diisocyanate (T.D.I.C.) reagent diluted from about 1-10 to about 1-40 times with dioxane, is added to the modifying group. The general procedure was disclosed by Singer and Schick, J. Biophysical and Biochem. Cytology 9:519 (1961). The amount of T.D.I.C. added may range from 0.075 to 1,000 molar equivalents of the modifier used. The reaction may be carried out at about −5° to about +10° C., preferably 0° to 4° C., for about ½ to 2 hours. Any excess T.D.I.C. may be removed by centrifugation. The precipitate may be washed with the above-mentioned phosphate buffer and the supernatants combined.

This activated modifying group solution may then be combined with the hormonal or non-hormonal polypeptide to be conjugated. Polypeptide is dissolved n the same phosphate buffer (5-30 mg/ml) and the volume of modifier and polypeptide combined according to the molar ratio of the two desired in the conjugate. Combined solutions are reacted at 30°-50° C., preferably 35°-40° C., for 3-6 hours.

Separation of modified polypeptide and free unconjugated polypeptide may be accomplished by conventional techniques, such as gel filtration.

Picogram amounts of $I^{125}$ labeled polypeptide may be added as a tracer to the reaction mixture at the time of conjugation, and a quantity of polypeptide conjugated to modifying groups (molar ratio) may be determined by the amount of radioactivity recovered.

Included in the methods for modifying the hormones, non-hormonal proteins and their fragments (unmodified polypeptides) are conjugation by use of water-soluble carbodiimide. The amino groups of the unmodified polypeptide are first preferably protected by acetylation. This (acetylated) unmodified polypeptide is then conjugated to modifier, such as natural protein modifier, e.g. hemocyanin from Keyhole limpet, homologous serum albumin, and the like, or Dextrans, Ficolls, or polytyrosine, preferably in the presence of guanidine such as guanidine HCl, using 10-ethyl-3-(3-dimethylamino propyl) carbodiimide as activating agent. This method is generally disclosed by Hoare and Koshland, Jr., J. of Biological Chemistry 242:2447 (1967). In the instance where Ficoll 70 is used, it is preferred that it be first treated with ethylene diamine so as to render the final coupling more efficient. This treatment with ethylene diamine may be performed in solvent such as saline and dioxane at about room temperature and a pH of about 9-12, preferably 10-11 for about ½ to about 2 hours. The conjugation itself between the umodified polypeptide and the modifier may be performed in solvent such as glycine methyl ester while maintaining the pH at about 4-5, preferably about 4.5-4.8. The temperature or reaction is conveniently about room temperature and the reaction may be allowed to proceed for about 2-8 hours, preferably 5 hours. The resulting modified polypeptide with which this invention is concerned may be purified by conventional techniques, such as column chromatography.

The immunogenic substances for this invention may also be provided by polymerization or unmodofied polypeptide using bifunctional imidoester. The imidoester, such as dimethyl adipimidate, dimethyl suberimidate and diethyl malonimidate, may be used to form the polymer in a manner similar to the generally described methods of Hartman and Wold; Biochem. 6:2439 (1967). The polymerization may take place conveniently at room temperature in aqueous solvent at a pH of about 9-12, preferably about 10-11, over a period of ¼-2 hours.

Said immunogenic substances may also be prepared by dimerization through a disulfide bond formed by oxidation of the thiol group on a Cys-residue using iodosobenzoic acid and methods corresponding to known methods, such as room temperature reaction for about 10-40 minutes.

Modified polypeptide may also be prepared using glutaric dialdehyde as conjugating agent. According to a theory proposed by Richards and Knowles [J. Mol. Biol. 37:231 (1968)], commercial glutaric dialdehyde contains virtually no free glutaric dialdehyde, but rather consists of a very complex mixture of polymers rich in $\alpha,\beta$-unsaturated aldehydes. Upon reaction with natural protein modifiers such as homologous serum albumins, these polymers form a stable bond through the free amino group, leaving aldehyde groups free. This intermediate product then reacts with unmodified polypeptide in the presence of alkali metal borohydride, such as sodium borohydride. This intermediate is formed at pH 7-10, preferably 8-9, at about room temperature. The modified polypeptide is also conveniently obtained at about room temperature after about ¼-2 hours' reaction time. The resulting product is recovered in pure form by conventional techniques, such as gel filtration, dialysis and lyophilization.

Polymerized sugar modifiers such as Ficoll 70 or Dextran T 70 may also be prepared for conjugation by treatment with a cyanuric halide such as cyanuric chloride to form a dihalotriazinyl adduct. The process may be performed in solvent such as dimethylformamide at about 0°-20° C., preferably 10°-15° C., for about ½-4 hours. The resulting intermediate product may then be dialyzed until essentially halogen ion free, and lyophilized and treated with unmodified polypeptide at pH 8-11, preferably about 9-10, for about ½-12 hours at about 15°-35° C., conveniently at room temperature. The resulting modified polypeptide may be recovered as indicated above.

Said polymerized sugar modifiers may also be treated with alkali metal periodate, such as sodium periodate, at a pH of 3-6 at about 30°-60° C. for about ½-4 hours, and the resulting intermediate conjugated with unmodified polypeptide at a pH of about 7-11, preferably about 8-10, for about ¼ to about 2 hours at a temperature of about 15°-80° C., preferably 20°-60° C. The resulting immunogenic substance according to this invention may be separated as indicated previously.

The modifying groups may vary in chemistry and number for any given polypeptide structure. However, they will attach to only certain amino acid moieties. In particular, when modifying with diazo groups they will chemically bond to only the histidine, arginine, tyrosine and lysine moieties or sites. Other modifying groups will bond to peptide molecules at different sites and in different numbers. Consequently, depending upon the size and chemical make-up of a particular modified polypeptide desired, one skilled in the art will readily be able to calculate the maximum possible number of modifying groups associable with a polypeptide. It is also recognized that several modifying groups may attach themselves to each other which in turn attach to a single amino acid moiety, but as used herein, reference to a number of modifying groups means the number of reaction sites to which a modifier has been attached.

As indicated above, a theory leading to this invention was that the chemical modification of an essential reproductive hormone would alter it such that it would exhibit antigenic properties so that when injected into an animal (including humans) it would cause the formation of antibodies which in turn would not only react to the injected modified hormone but also to the natural unmodified endogenous hormone as well. With this theory in mind, reproductive hormones of various species were modified and tested in baboons. The results illustrated that modified hormones of unrelated species do not produce the desired results, whereas modified hormones of the same or closely related species do produce the desired results. It will accordingly be clear that the polypeptide to be modified should be so related to the endogenous hormone or non-hormonal protein so as to be either from the same animal species or be the immunological equivalent thereof as modified.

Additional experiments were conducted to test the validity of this concept in humans, i.e. modified human reproductive hormones injected into humans. Collectively, the results prove the conclusion drawn from the experiments with the baboons, namely, isoantigenic immunization using modified human reproductive hormones does produce contraception or interruption of gestation. Detailed examples which follow illustrate this result.

It is known that fragments of endogenous hormones exhibit essentially no antigenic properties. However, should a large enough fragment of an endogenous hormone be slightly modified as indicated above, then antibodies will be formed which will react in the same way as if the modification is on a whole hormone, provided the large fragment is sufficiently distinctive in chemical and physical make-up as to be recognized as a specific part of the whole.

Whether the hormone or specific fragment thereof is naturally occurring or is a synthetic product is clearly immaterial. A synthetic hormone molecule will perform the same function as the naturally occurring one, being equivalent for the purpose of this invention. In this connection, it will be noted that natural substances with which this invention is concerned possess carbohydrate moieties attached at certain sites thereof whereas the contemplated corresponding synthetic polypeptides do not. Nevertheless, for the purpose of the instant specification and claims, the synthetic and natural polypeptides are treated as equivalents and both are intended to be embraced by this invention. Reference in the above regard is made to Table No. 3 herein as read in conjunction with Example XXIX.

Thus, where the word "hormone" or "hormone molecule" is used herein, the word "synthetic" may be added before "hormone" without changing the meaning of the discussion. Similarly, the word, "fragment" may be inserted after "hormone" or "molecule" without changing the meaning, whether or not "synthetic" has been inserted before "hormone".

Throughout the above specification, the term "modified" has been utilized in referring to the chemical reaction by which the foreign molecules become chemically attached to specific sites on the usually much larger polypeptide molecule. Although specific mechanisms by which this is accomplished are described herein in detail, other appropriate mechanisms may be used if desired. It is clear that the modifier, i.e., the substance which modifies the concerned protein, can be a physically larger molecule or fragment thereof than the molecule or fragment which it modifies. As noted above, such large molecules are deemed herein to be "carriers". Clearly, physical size of the fragment is not always critical; the criterion for effectiveness being that the body reaction generate antibodies in sufficient quanta and specific to the targeted hormone or endogenous substance.

The modified polypeptides of this invention may be administered parenterally to the animals to be protected, preferably with a pharmaceutically acceptable injectable vehicle. They may be administered in conventional vehicles with other standard adjuvants, as may be desirable, in the form of injectable solutions or suspensions. As indicated earlier, the adjuvant serves as a substance which will elevate total immune response in the course of the immunization procedure. Lipasomes have been suggested as suitable adjuvants. The insoluble salts of aluminum, that is, aluminum phosphate or aluminum hydroxide, have been utilized as adjuvants in routine clinical applications in man. Bacterial endotoxins or endotoxoids have been used as adjuvants as well as polynucleotides and polyelectrolytes and water soluble adjuvants such as muramyl dipeptides. The adjuvants developed by Freund have long been known by investigators, however, the use thereof is limited to non-human experimental procedures by virtue of a variety of side effects evoked. The preferred mode of administration of the entire vaccine is intramuscular.

The amount of modified polypeptide to be administered will vary depending upon various factors, including the condition being treated and its severity. However, in general, unit doses of 0.1–50 mg in large mammals administered one to five times at intervals of one to five weeks provide satisfactory results. Primary immunization may also be followed by "booster" immunization at one to twelve month intervals.

DESCRIPTION OF THE PREFERRED EMBODIMENTS

EXAMPLE I

Adult female baboons were studied for at least one menstrual cycle for patterns of urinary estrogens, plasma, progestin, and in some cases urinary LH. Only those animals displaying normal patterns of these hormones were immunized. The criteria for normality and the procedures for housing animals are well known and will not be described.

Gonadotropin Preparations

Human Luteinizing Hormone (HLH)—partially purified preparation from human pituitaries with a biological potency of 2.5 units per mg. (NIH-LH-SI).

Human Follicle Stimulating Hormone (HFSH)—a partially purified preparation from humand pituitaries with a biological potency of 86 units per mg. (NIH-FSH-SI).

Human Chorionic Gonadotropin (HCG)—a highly purified preparation from human pregnancy urine with biological potency of 13,200 IU/mg. (2nd IRP-HCG).

Monkey Luteinizing Hormone (MLH)—a crude preparation from rhesus monkey pituitaries with a biological potency of 0.75 units per mg. (NIH-LH-SI).

Ovine Luteinizing Hormone (OLH) (NIH-LH-S5).

Baboon Luteinizing Hormone (BLH)—partially purified baboon pituitary preparation with a biological potency of 1.1 units per mg. (NIH-LH-S1).

All preparations, excepting the OLH, were prepared in the inventor's laboratory. LH and HCG biological activity was determined by the ovarian ascorbic acid depletion test and the FSH preparation assayed by the ovarian augmentation assay.

Hormones were altered as antigens by coupling with a hapten in varying ratios of hapten to hormone as described by Cinader et al., supra. For convenience, the Cinader process is discussed herein although Phillips, supra, may provide a more stable bond under certain circumstances. In this procedure, the protein hormone serves as a carrier and the hapten is coupled to it by diazo bonds. Although a variety of hapten groups were coupled to different hormones, the same basic procedure was used for any combination. Fifteen to thirty-five haptenic groups per hormone molecule were found most useful for preparing immuizing antigens. The basic reaction consisted of diazotizing the hapten (sulfanilic acid) by adding it to a solution of 0.11 N HCl and then slowly adding this solution dropwise to a 1 percent solution of $NaNO_2$ with constant stirring at 4° C. Diazotization was considered complete with free $HNO_2$ was detected in the reaction mixture. Although the above reaction was accomplished at 4° C., optimum temperatures for the reaction normally are about 0°–6° C., although 4° C. is preferred.

The hapten-protein coupling was performed by dissolving the protein hormone in an alkaline buffer, pH 8.0. The diazotized hapten was added slowly to the hormone solution with continuous stirring at 4° C. The pH of the reaction was constantly monitored and kept near 8.0. After all the hapten was added, the pH was finally adjusted to 8.0, stirred for 1–2 hours and allowed to stand at 4° overnight. The mixture was thoroughly dialyzed for 6–8 days against distilled water to remove unreacted hapten.

Although the number of diazo groups per hormone molecule could be regulated by the number of moles of hapten and hormone reacted, a parallel control experiment with $S^{35}$ labelled sulfanilic acid to evaluate the precise composition of the haptenprotein samples was performed with each diazotization. The same hormone preparation to be used for immunization was used in the control experiment. After the reaction was completed, an aliquot was taken from the reaction mixture and the remainder thoroughly dialyzed. Equal volumes of the dialyzed and undialyzed solutions were counted by liquid scintillation. By comparing the counts of the dialyzed and undialyzed samples, the moles of hapten coupled to each mole of hormone was calculated since the unreacted hapten was removed by dialysis. For this calculation, a molecular weight of 30,000 was assumed for all gonadotropin preparations.

Following dialysis, hapten-hormones were lyophilized and stored at 4° C. Diazo-HCG (35 groups/-molecule) and HLH (26 groups/molecule) were bioassayed by the ovarian ascorbic acid depletion method and found to retain 62 and 85 percent respectively of the activity of the unaltered hormones from which they were derived. None of the other hormones were assayed for biological activity.

Immunization Procedures

Female baboons received their initial immunization on days 3–5 of the menstrual cycle and the second and third injections one week apart. The fourth injection was given 2–3 weeks after the third. A few animals received a fifth injection at 70–80 days after the first injections. All antigens were administered subcutaneously in a suspension of mannide manoleate or peanut oil. Doses of antigens for each injection varied between 3 and 5 mg. Injection sites were inspected daily for 5 days after each immunization for local reactions.

Monitoring Effects of Immunization.

Daily 24-hour urine specimens and frequent serum samples were collected during at least one menstrual cycle prior to immunizations and following immunizations until the effects of treatment were assessed. Urinary LH, urinary estrogens and plasma progestins were measured. Antibodies were detected in post-immunization serum samples by reacting 0.2 ml. of a 1:1000 dilution of serum in phosphate-buffered saline (pH 7.4) 0.5 percent normal baboon serum with 250 pg of $1^{131}$ labelled hormone. Sera were reacted with both the unaltered immunizing hormone and unaltered baboon LH for antibody detection. A purified baboon LH preparation (1.9×NIH-LH-S1) was used as a tracer antigen. Antigen-antibody complexes were precipitated with ovine anti-baboon gamma globulin after a 24-hr. incubation at 4° C. Antibody levels were expressed as pg of labelled hormone bound. Significant antibody levels were considered to be those that would bind 5.0 pg or more of the $1^{131}$ labelled antigen.

Antisera were fractionated by gel filtration of Sephadex G-200 according to the procedure of Fahey and Terry (at p. 36, Experimental Immunology, F. A. Davis Co., Philadelphia, Pa., 1967, incorporated by reference to the extent necessary to understand the invention) to determine the proportion of IgM and IgG antibodies in the baboon sera. Since the IgG fraction in this procedure contained a portion of IgA and IgD antibodies, only IgM and total titers were determined. The IgM fraction from the column was reacted with $1^{131}$ hormones and the binding capacity determined. The volumes of the fractionated sera were adjusted so that antibody levels would be comparable to those of whole serum.

Antibody Production

No significant reactions were observed at the site of injection following any immunization. On 4 occasions, a slight induration (2–3 cm in diameter) was seen when mannide manoleate was used as a vehicle but the redness and swelling disappeared within 4–5 days. Antibodies were detected against the immunizing antigen within 3–5 weeks in all animals. The extent, duration and cross reactivity of these antibodies is recorded. Generally speaking, higher levels were observed to heterologous gonadotropin immunization than to homologous ones.

The cross-reactivity of induced antibodies with baboon LH was studied on each animal. Cross-reactivity of antisera at peak levels was recorded. Although relatively high antibody activity against human LH and HCG were seen, relatively little reaction with baboon LH occurred. An intermediate cross-reaction was noted with anti-ovine LH and a high degree of cross-reactivity was seen with anti-monkey LH. Diazo-human FSH was weakly antigenic in the baboon. The duration of antibody production was generally longer with the human and sheep gonadotropin immunization than with those of monkey or baboon origin.

Peak antibody levels usually occurred at the time when the antibodies had shifted to principally the IgG type. Early antibodies had a larger proportion of IgM type and were generally more cross-reactive with baboon LH. The change in the proportion of the total antibody population that was IgM was recorded from the time antibodies were first detected. Significant cross-reactivity to baboon LH was observed in anti-human gonadotropins when IgM was abundant but dropped sharply as the antisera shifted to nearly all IgG. This drop in cross-reactivity did not occur with monkey and baboon immunizations. Again, the ovine LH immunizations produced an intermediate change in reactivity with the shift from IgM to IgG.

Effects on the Menstrual Cycle

The effects of immunization upon the event of the menstrual cycle were determined by observing changes in sex skin turgescence and levels of pituitary and/or ovarian hormones. Based on these parameters, the delay or retardation of ovulation from the expected time, as judged by the control cycle, was calculated. One animal immunized with HCG had no interruption in ovulation and another immunized with HFSH was delayed for only one cycle. Two animals injected with HLH and two injected with HCG had ovulation delays equivalent to two menstrual cycles. A third animal immunized with HLH was delayed a calculated 86 days. Ovine LH immunizations produced an 88 day delay in ovulation.

Immunizations with diazo-monkey or baboon LH resulted in longer disruption of the menstrual cycle. Calculated delays in ovulation for the two animals receiving monkey LH was 146 and 122 days whereas the animals receiving altered baboon LH were retarded from ovulation 224 and 210 days.

Effects on specific hormone patterns following immunization with HLH in one animal were recorded. The interval between menses was considered to represent a "cycle". Urinary estrogens and plasma progestin patterns indicated that no ovulation occurred during the cycle of immunization which was 85 days in duration. Urinary estrogens were elevated during treatment but did not reflect a typical pattern. Plasma progestins were not elevated until about day 19 of the final post-treatment cycle. Patterns of both estrogens and progestins were within normal limits during the second post-treatment cycle. Antibody levels were elevated from about day 35 of the treatment cycle until 289 days from the first detection of antibodies. An LH assay was not available when this animal was studied and no data on plasma or urinary levels of this hormone was obtained.

Hormonal patterns following an immunization with diazobaboon LH were recorded. In this animal, antibody levels were lower and persisted, in general, for a shorter period than did immunizations with human gonadotropins. During the treatment cycle, levels of urinary estrogens and plasma progestins followed a normal pattern but were quantitatively lower than normal. Urinary LH patterns fluctuated markedly due to the injections of diazo-LH during this period. No conclusive evidence of ovulation was obtained for the treatment cycle. The first post-treatment cycle lasted 246 days. During this cycle urinary LH and estrogens were elevated on days 35-41 but there was no subsequent elevation in plasma progestins that would indicate ovulation had occurred. Following day 42 of this cycle, there was no significant elevation in any of the three hormone levels until day 231 when significant elevations of urinary estrogens and LH occurred. These rises were followed 3 days later by an elevation in plasma progestins indicating the presence of a functioning corpus luteum. A second post-treatment menstrual cycle was of normal duration and the endocrine patterns were normal.

Antibodies to unaltered baboon LH attained maximum levels by about day 70 of the post-treatment cycle and remained relatively constant until day 190 when a steady decline was observed. By day 215 of this cycle, antibody levels were barely detectable. Approximately 16 days after this time, a peak of LH commensurate with a normal midcycle elevation was observed. From this point the animal appeared to have the normal function of the pituitaryovarian axis. Hormonal patterns in animals with other heterologous gonadotropin immunizations were similar to animal receiving HLH and other animals receiving monkey or baboon LH were similar in response to animal receiving baboon LH.

These results in baboons indicated that the modification of a reproductive hormone, by the procedures outlined, did render it antigenic and the antibodies thus formed did neutralize natural endogenous hormones if the natural hormone was obtained from the species receiving the immunizations with modified hormone.

EXAMPLE II

HCG is a hormone naturally present only in pregnant women with the exception that an entity at least analogous thereto has been found to be present in humans in conjunction with neoplasms. HCG is also commercially available. Human LH is immunologically and biologically identical to HCG, even though there are chemical differences. Since they are biologically identical and HCG is readily available from commercial sources it was presumed that the effectiveness of this immunological procedure could be evaluated by injecting modified HCG into non-pregnant women and monitoring the blood levels of LH. Antibodies formed will neutralize both the LH and the modified HCG. Reference in the above regard is made to the publications identified earlier herein.

Women have a pattern of LH levels; the level is substantially constant until the middle period between menstrual cycles, immediately prior to ovulation; at that point the LH level rises greatly and helps induce the ovulation. Monitoring the LH level and the antibody level will show that the procedure used did or did not cause the production of antibodies capable of neutralizing the endogenous reproductive hormone, namely LH.

A women aged 27 years was selected for study. Hormone was obtained, purified and modified. The modified human hormone (HCG) was injected into the subject. It is well known that antibodies to HCG react identically to LH as well as HCG. The effect of the immunization was evaluated, principally by monitoring blood levels of LH. Finally the results were evaluated.

Preparation of Hormone

Clinical grade HCG derived from pregnancy urine was obtained from the Vitamerican Corp. Little Falls, N.J. This material has an immunological potency of 2600 IU/mg. Contaminants were detected in this preparation. Purification consisted of chromatography and elution. Fractions were dialyzed and lyophylized. The most potent fraction contained approximately 7600 IU/mg., however, it was heterogenous on polyacrylamide gel electrophoresis.

The fraction was further purified by gel filtration. The elution profile revealed two major protein peaks. The most potent HCG was found in the first peak and had an immunological potency of 13,670 IU per mg. This fraction was subjected to polyacrylamide gel electrophoresis. Further purification by gel filtration showed no evidence of heterogeneity of the HCG at this stage. Consequently, materials for study were processed according to the above procedure.

The contamination of this purified HCG was tested with $I^{131}$ used for identification and a sample was reacted with antisera against several proteins offering potential contamination. Those proteins were follicle stimulating hormone, human growth hormone, whole human serum, human albumin, transferin, alpha one globulin, alpha two globulin and orosomucoid. No detectable binding of the purified HCG was observed with any antisera at a dulution of 1:50 of each. These negative results, calculated against potential binding of the respective proteins, indicated that contamination with any was less than 0.005 percent.

Alteration of Hormone

Hormone was altered by coupling with a hapten (sulfanilazo). This method couples the hapten molecules to the protein via the amino group of the aliphatic or aromatic portion of the hapten. The number of hapten molecules coupled to each HCG molecule (Ha-HCG) can be regulated and for this study, forty haptenic groups per HCG molecule were used for preparing the immunizing antigen.

Following the hapten-coupling process, the Ha-HCG was sterilized and tested.

Subject

The subject was multiparous and had terminated her reproductive capabilities by prior elective bilateral salpingectomy. She was in good health and had regular cyclic menstruation. She underwent complete history, physical examination and laboratory evaluation including blood count, urinalysis, latex fixation and Papanicolau smear. She had no history of allergy.

To demonstrate normal functioning of the pituitaryovarian axis prior to immunization, blood samples were obtained every other day from the first day of menses for 10 days, then daily for 10 days and finally, every other day until the next menses. Serum determinations of FSH, LH, estrone, estradiol and progesterone were performed. These studies indicated an ovulatory pattern.

Immunization Procedures

Ten mg. of the Ha-HCG antigen were dissolved in 1.0 ml. of saline and emulsified with an equal volume of oil. Prior to injection, scratch tests to antigen and vehicle were performed. Immunizations were begun in the luteal phase of the treatment cycle to prevent superovulation from the administered HCG. Four injections at two week intervals were given to the subject. The first two of these were administered in oil subcutaneously (1.0 ml. in each upper arm); the final two injections were given in saline only via the intradermal route. Following each injection, blood pressure readings were taken and the subject observed for allergic reactions.

Monitoring Effects of Immunizations

Blood samples were collected at weekly intervals beginning two weeks after the initial injection to test for the presence of humoral and cellular antibodies. Following completion of the immunization schedule, blood samples were collected in the same manner as in the control cycle to assess effects of immunization on hormonal patterns of the menstrual cycle. Since antibodies to HCG react identically to LH as with HCG, LH was monitored as an index of effectiveness of the procedure. A third cycle was similarly studied six months after initial immunization. Upon completion of the study, physical and pelvic examinations and laboratory evaluations were repeated.

Serum samples from the control and post-treatment cycles were assayed for FSH, LH, estrone, estradiol and progesterone.

The subject was tested for delayed hypertensivity before immunization and at two week intervals until the injection schedule was completed by an in vitro lymphocyte transformation test.

Results

Temporal relationships of serum pituitary and gonadal hormones in the control cycles of the subject were recorded. Antibody titers to HCG were detected in the subject after two injections. Menses occurred at regular intervals during the immunizations.

Following the initial injection in mannide manoleate, some itching and swelling at the injection site occurred. Subsequent intradermal injections in saline produced no reactions and it was concluded that the local reactions were induced by the mannide manoleate. Lymphocyte transformation tests on plasma samples were negative.

In the post-treatment cycle, baseline follicular and luteal phase LH levels were not noticeably changed in the subject. Very small midcycle elevations in LH levels were observed as compared to the normal large increases. FSH patterns in the post-treatment cycle were normal. This indicated that the antibodies were neutralizing the action of endogenous LH.

The subject showed an ovulatory progesterone pattern but attained relatively high antibody titers to LH and HCG after only two injections of Ha-HCG.

The subject was studied during another cycle approximately six months from the first immunization. Significant antibody titers were found. LH patterns indicated a small midcycle elevation. FSH patterns were essentially normal. Thus, the specificity of anti-HCG antibodies to LH was shown but not to FSH.

EXAMPLE III

Another woman aged 29 years was selected for further study. Hormone was obtained, purified, and modified as in Example II. This modified hormone was injected into this subject in the same way as in Example II. The subject was monitored and tested as in Example II.

The results were similar to the results found in Example II except that (1) the levels of estrone and estradiol were substantially normal, (2) the subject acquired significant antibody titers late in the post-immunization cycle, and (3) in the cycle studied after six months this subject showed no significant midcycle elevation in LH patterns.

EXAMPLE IV

Anther woman aged 29 years was selected for further study. Hormone was obtained and purified and modified as in Example II. This modified hormone was injected into this subject in the same way as in Example II. The subject was monitored and tested as in Example II.

The results were similar to the results found in Example II except that (1) baseline follicular and luteal phase LH levels were noticeably depressed in the post-treatment cycle, (2) no midcycle elevations were observed in LH, (3) estrone levels were elevated during the follicular phase of the post-immunization cycle, and (4) during the six-months study there was no significant midcycle elevation in LH patterns.

EXAMPLE V

Another woman aged 35 years was selected for further study. Hormone was obtained, purified, and modified as in Example II. This modified hormone was injected into this subject in the same way as in Example II. The subject was monitored and tested as in Example II.

The results were similar to the results found in Example II except that (1) baseline follicular and luteal phase LH levels were noticeably depressed in the post-treatment cycle, (2) a very small midcycle elevation of LH were observed, (3) levels of FSH patterns in the post-treatment cycle were depressed, and (4) levels of both estrone and estradiol were reduced, during the follicular phase of the post-immunization.

EXAMPLE VI

Another woman aged 28 years was selected for further study. Hormone was obtained, purified, and modified as in Example II. This modified hormone was injected into this subject in the same way as in Example II. The subject was monitored and tested as in Example II.

The results were similar to results found in Example II except that (1) baseline follicular and luteal phase LH levels were depressed in the post-treatment cycle, (2) no peaks were observed in midcycle levels of LH, (3) estrone levels appeared elevated in the follicular phase of the post immunization cycle, and (4) LH patterns indicated no significant midcycle elevation in the six-month post-immunization cycle.

EXAMPLE VII

Another woman aged 28 was selected for further study. Hormone was obtained, purified, and modified as in Example II. This modified hormone was injected into this subject in the same way as in Example II. The subject was monitored and tested as in Example II.

The results were similar to results found in Example II except that (1) antibody titers to HCG were not detected until after three injections, (2) baseline follicular and luteal phase LH levels were depressed in the post-treatment cycle, (3) no peaks nor midcycle elevation in the LH were observed, (4) estrone levels were elevated during the follicular phase, and (5) no significant antibody titers were found in the six-month cycle.

All the above examples show the practicality of injecting modified hormonés for the purpose of neutralizing an endogenous reproductive hormone and thereby offering a procedure for the prevention of conception or the disruption of gestation.

EXAMPLE VIII

Data obtained in earlier experiments and discussed in Examples I–VII showed that a modified natural reproductive hormone, when injected into an animal of species from which it was derived, would produce antibodies that would neutralize the action of the unmodified endogenous natural hormone in the body of the animal. Hormones used in Examples I–VII were FSH, LH and HCG. New experiments were performed, baed on this knowledge, to identify another reproductive hormone (placental lactogen) that could be used in a similar fashion.

Preparation of Hormone

A purified preparation of placental lactogen was prepared from placentae of baboons since it was intended to use modified placental lactogen to immunize baboons. Placentae were extracted and purified on column chromatograph according to previously published procedures. The purity was tested by polyacrylamide gel, electrophoresis and by radioimmunoassay. The material obtained showed a high degree of purity on electrophoresis and radioimmunoassay showed no contamination with other placental hormones.

Hormone Modification and Immunizations

The baboon placental lactogen (BPL) was altered by coupling with the diazonium salt of sulfanilic acid as outlined for other hormones in Example I. The number of diazo molecules per BPL molecule in this instance was 15. Immunization procedures were also similar to those described in Example I for other hormones.

Results

Within 4–6 weeks after the first injection of diazo-BPL, antibody levels to natural unmodified BPL in vitro were detected in 6 female baboons. Levels rose to a plateau within 8–10 weeks and remained there for several months. Hormonal measurements indicated that there were no efects on the normal events of the menstrual cycle due to the immunizations. Since BPL is normally secreted only in pregnancy, this was not a surprising observation.

All six females were mated with a male of proven fertility three times (once each in three different cycles during the fertile period). Pregnancy diagnosis by hormonal measurement was performed after each mating. From the 18 matings, there were 13 conceptions as judged by pregnancy tests. The animals that were pregnant had menstrual bleeding 7–12 days later than was expected for their normal menstrual cycles. Subsequent hormonal measurements confirmed that these 13 pregnancies were terminated by abortions approximately one week after the time of expected menses.

These findings suggest that the antibodies formed in the animal's body after immunization had no effect on the nonpregnant menstrual cycle but when pregnancy was established, they neutralized the baboon placental lactogen in the baboon placenta and the result was abortion very early after conception.

When in Examples I–VIII above Structures (I), (II), and (III) are modified by use of diazosulfanilic acid, dinitrophenol, or S-aceto mercaptosuccinic anhydride or Structures (II), and (III) are modified by addition of polytyrosine or polyalanine, according to known methods, the results obtained should be similar to those in said Examples.

Similarly, when FSH, somatomedian, growth hormone or angiotension II are modified by use of diazosulfanilic acid or trinitrophenol, the results obtainable upon administration of the purified modified polypeptide into a male or female human or animal would indicate the stimulation of antibodies which neutralize all or some of the modified polypeptide as well as corresponding endogenous polypeptide.

EXAMPLE IX

The subjects used in the studies reported in the example are female baboons. All baboons were adults of reproductive age. A description of subjects and the conditions of experimentation have been described in Example I. The animals have been studied using highly purified beta subunits of HCG using a preparation with a biological activity of less than 1.0 IU/mg. Animals were immunized with 14–26 moles/mole of polypeptide of diazosulfanilic acid coupled subunits in mannide manoleate.

Antibody levels were assessed by determining the binding of serum dilutions with $I^{125}$ labelled antigens. Crossreactivity of antisera was measured by direct binding of labelled antigens and by displacement radioimmunoassays. Antifertility effects in actively immunized animals were tested by mating females with males of proven fertility. Effects in pregnant baboons passively immunized with either sheep or baboon anti-β-HCG were determined by monitoring serum levels of gonadotropins and sex steroid hormones before and after immunizations.

Eight female baboons were immunized with the modified beta subunit of HCG. Significant antibody levels were attained in all animals.

Baboon immunizations with the modified beta subunit of HCG resulted in high antibody levels reacting to HCG, human LH and baboon CG but not to baboon LH. All animals remained ovulatory, however, no pregnancies resulted from numerous matings with males of proven fertility. Passive immunization of non-immunized pregnant baboons with sheep anti-β-HCG serum produced abortions within 36–44 hours.

EXAMPLE X

Hemocyanin from Keyhole limpet (KLH) solution (7 mg/ml) in 0.05 M sodium phosphate buffer in 0.2 M NaCl, pH 7.5, is prepared. Insoluble particles are removed by centrifugation. To one ml of this solution, tolylene diisocyanate (T.D.I.C.) reagent is added (20 μl) diluted to 1/30 with dioxane, the amount being essentially the equivalent of the moles of lysyl residues in the KLH molecules. After 40 minutes at 0° C., the T.D.I.C. activated KLH solution is combined with 0.5 mg of synthetic β-HCG peptide having the following structure:

Asp-His-Pro-Leu-Thr-Cys-Asp-Asp-Pro-Arg-Phe-
Gln-Asp-Ser-Ser-Ser-Ser-Lys-Als-Pro-Pro-Pro-
Ser-Leu-Pro-Ser-Pro-Ser-Arg-Leu-Pro-Gly-Pro-
Pro-Asp-Thr-Pro-Ile-Leu-Pro-Gln-Ser-Leu-Pro

Structure (XV)

which is first dissolved in 25 μl of 0.05 M sodium phosphate buffer in 0.2 M NaCL, pH 7.5. The mixture is incubated at 37° C. for four hours. The resulting product is purified by gel filtration.

EXAMPLE XI

One g. of Ficoll 70 is dissolved in 1 ml each of normal saline and 2 M ethylene diamine (adjusted to pH 10 with hydrochloric acid) solution. The solution is kept at room temperature in a water bath and stirred with a magnetic stirrer. Cyanoger bromide, 4 g, dissolved in 8 ml of dioxane, is added to the Picoll 70 solution. The acidity of the mixture is maintained at pH 10–10.5 for 8 minutes by adding drops of 2 N sodium hydroxide solution. An additional 2 ml of 2 M ethylene diamine, pH 10, solution is added, and stirring at room temperature is continued for 30 more minutes. The product is purified by passing it through a Bio-Gel p-60 column.

EXAMPLE XII

Two mg of the compound of Structure (II) containing picogram amount of $I^{125}$ labeled adduct and KLH (1.6 mg) is dissolved in 1 ml. of 1.0 M glycine methyl ester in 5 M guanidine hydrochloride. Ethyl dimethylamino propylcarbodiimide (E.D.C.) 19.1 mg is added to this solution. The acidity is adjusted to and maintained at pH 4.75 with 1 N HCl at room temperature for 5 hours. The KLH-peptide conjugate is purified by passing it through a Bio-Gel p-60 2.2×28 cm column equilibrated with 0.2 M NaCl.

EXAMPLE XIII

Solid bifunctional imidoester dihydrochloride (3 mole) is added in 2 mg portions at 5-minute intervals to a constantly stirred solution of 1 mole of polypeptide of Structure (II) (1–20 mg/ml) in 0.1 M sodium phosphate, pH 10.5, at room temperature. Sodium hydroxide 0.1 N is added to maintain the acidity at pH 10.5. One hour after the addition of the diimidoester has been completed, a polymerized product according to this invention is obtained.

EXAMPLE XIV

To a 20 mg/ml solution of homologous serum albumin in 0.1 M borate buffer, pH 8.5, 1000% mole excess of 25% aqueous solution of glutaric dialdehyde is added at room temperature. The excess dialdehyde is removed by gel filtration in water using Bio-Gel p-2. The material collected at the void volume is lyophilized, and the dried product is redissolved in 0.1 M borate buffer, pH 8.5 (20 mg/ml), mixed with the required amount of polypeptide of the following Structure:

Asp-Asp-Pro-Arg-Phe-Gln-Asp-Ser-Ser-Ser-Ser-
Lys-Als-Pro-Pro-Pro-Ser-Leu-Pro-Ser-Pro-Ser-
Arg-Leu-Pro-Gly-Pro-Pro-Asp-Thr-Pro-Ile-Leu-
Pro-Gln-Ser-Leu-Pro

Structure (XVI) (20 mg/ml) in the same buffer at room temperature. Twenty minutes later, sodium borohydride in 250 percent molar excess of polypeptide XVI is added. The reaction is terminated after one hour. The conjugated product is purified by gel filtration on Bio-Gel p-60 column, dialyzed free of salt and lyophilized.

EXAMPLE XV

Ficoll 70 1 g, $NaHCO_3$ 500 mg, cyanuric chloride 3 g, $H_2O$ 20 ml, and dimethylformamide 80 ml., are stirred at temperature below 16° C. for 2 hours. The product is dialyzed against distilled water until Cl-free, then lyophilized. A polypeptide of Structure (XV) (2 mg) containing minute quantity of $I^{125}$-labeled analogue is incubated with 1 mg of this product in 0.25 ml of 0.2 M sodium borate buffer, pH 9.5, for one hour at 20° C., and the product is recovered from a Bio-Gel p-60 2.2×28 cm column.

When the above procedure is carried out and Dextran T 70 is used in place of Ficoll 70, the corresponding modified polypeptide, useful according to this disclosure, is obtained.

EXAMPLE XVI

Ficoll 70 1 g, $NaIO_4$ 1.2 g, and KCl 0.42 g are dissolved in 1.5 ml of 1 M sodium acetate buffer, pH 4.5, and incubated at 37° C. for 1 hour.

Two mg (=588 μmoles) of polypeptide of Structure (XV) above mixed with a minute quantity of $I^{125}$-labeled analogue is incubated with 2 mg of the product obtained above in 0.3 ml of 0.2 M borate buffer, pH 9.5 at 55° C. for 1 hour. The reaction mixture is then chilled in an ice water bath and $NaBH_4$ 1 mg is then added into this solution. The reduction reaction is terminated by passing the product through a Bio-Gel p-60 2.2×28 cm column equilibrated and eluted with 0.2 M NaCl.

EXAMPLE XVII

Numerous rabbits are immunized with a variety of synthetic peptides conjugated to different modifying groups. Following two or three immunizations at 3–5 week intervals, sera from animals are assessed by determining their ability to bind in vitro to radiolabeled HCG. The specificity of this binding is studied by reacting the same sera against similarly labeled other protein hormones, particularly, pituitary LH. Sera are further assessed by determining their ability to inhibit the biological action of exogenously administered HCG in bioassay animals. Thus, the increase in uterine weight of the immature female rat in resonse to a prescribed dose of HCG is noted.

The dose of HCG is administered subcutaneously in saline in five injections over a three day period and the animal is sacrificed for removal of the uterus on the fourth day. The weight of the uterus increases in dose reponse fashion to the hormone injections. When assessing the effects of antisera in this response, varying quantities of test serum are administered intraperitoneally separately from the subcutaneous injection of hormone during the assay. This procedure permits the antiserum to be absorbed rapidly into the rat's bloodstream and will permit interaction of it with hormone when the latter likewise enters this fluid. If the antiserum is capable of reacting with the hormone in a manner preventing stimulation of the uterus, the antiserum is considered to be effective for biological inhibition of hormone action.

The frequency of animals showing a positive response to immunological binding and neutralization of biological activity is presented in

EXAMPLE XVIII

Iodosobenzoic acid dissolved in a slight excess of 1 N potassium hydroxide in 10% molar excess is added to the peptide of Structure (II) in phosphate buffer with normal saline at pH of 7.0. After thirty minutes at room temerature, the product polypeptide dimer is purified by gel filtration.

EXAMPLE XIX

To an ice water bath cooled and vigorously stirred 0.23 ml. of bovine gamma globulin (10 mg/ml) in 0.05 M phosphate buffer with normal saline (PBS) pH 7.5, 50 μl of 1/10 T.D.I.C. in dioxane is added. After 40 minutes, in excess T.D.I.C. is removed by centrifugation (0° C., 10 minutes, 10,000 g) and the precipitate is washed twice with 0.1 ml. of PBS. The combined supernatents are added to 7.7 mg. of the peptide of Structure (II) dissolved in 0.8 ml. of PBS, pH 7.5. The mixture is stirred at room temperature for 10 minutes, then incubated at 37° C. for 4 hours. The conjugate product is purified by dialysis.

EXAMPLE XX

BSA (10 mg/ml) in PBS solution (0.25 ml.) is treated with 50 μl of 1/10 T.D.I.C. dioxane solution and conjugated to 7.5 mg. of synthetic β-HCG peptide of Structure (III) in 0.8 ml. of PBS (pH 7.5) as in Example XIX to obtain the product.

EXAMPLE XXI

To an ice water bath cooled and vigorously stirred 0.6 ml. of β-HCG peptide of Structure (III) (10 mg/ml) in phosphate buffered saline, pH 7.5, is added 30 μl of 1/10 T.D.I.C. After 40 minutes, the excess T.D.I.C. is removed by centrifugation (10,000 g, 0° C., 10 minutes) and the precipitate is washed twice with 0.1 ml. PBS. The combined supernatents are added to 3 mg. of poly (D, L-Lys-Als) dissolved in 0.3 ml. of PBS. The mixture is incubated at 37° C. for 4 hours. The product is then dialyzed and lyophilized.

EXAMPLE XXII

The results set out in Table I provide further evidence of the broad applicability of this invention as indicated previously in this specification.

Using standard methods of testing in rabbits, both immunological binding response and neutralization of biological activity were established for the medified polypeptides indicated with the result as set out in Table I.

EXAMPLE XXIII

Antigen was prepared by reacting a Diisocyanate (T.D.I.C.—see above) coupling reagent with carrier (tetanus toxoid), extracting excess reagent and incubating activated carrier with peptide Structure (II). Baboons were immunized with the antigen and the results of mating 4 animals three times are shown in FIG. 1. The figure shows that from 12 exposures (matings) one pregnancy resulted even though relatively low levels of immunity from the antigen were achieved. Non-immunized baboons of the same colony had a fertility rate of approximately 85%.

EXAMPLE XXIV

Referring to FIG. 2, baboons were immunized initially with a beta subunit of HCG modified by diazotization in a manner similar to that described in conjunction with Example II. Following this initial administration, the baboons were injected 21 and 42 days later with Structure (II) above having been modified by the same diazotization process. FIG. 2 shows plots representing the levels of antibodies generated in consequence of these administrations. Such quantities of antibodies are expressed as micrograms of isotopically-labeled HCG that will bind each milliliter of serum from the baboons at specified days after the initial injection. The levels shown were maintained for a period of over one year.

TABLE 1

Frequency of Positive Antibody Responses to Various HCG Peptide-Conjugates

| | | Number of Rabbits | | |
|---|---|---|---|---|
| Peptide | Carrier | Immunized | Immunological Binding Responses | Neutralization of Biological Activity |
| 35 amino acid 111-145 | Bovine Gamma Globulin | 10 | 10 | 6 |
| Morgan et al Peptide II | Keyhole Limpet Hemocyanin | 10 | 5 | * |
| 31 amino acid 115-145 | Poly-D-L-Alanine | 10 | 9 | 5 |
| Morgan et al Peptide III | Bovine Serum Albumin | 12 | 12 | 6 |
| 44 amino acid 105-148 | Keyhole Limpet Hemocyanin | 10 | 8 | * |
| Peptide XV | | | | |
| Natural 109-145 Keutman Peptide XII | Keyhole Limpet Hemocyanin | 10 | 10 | * |

*additional time needed for assessment

Referring to Table 2, the results of breeding the two baboons represented in FIG. 2 is revealed in tabular form. The table presents the results of mating these animals ten times over a period of approximately one year. These data suggest that the animals ovulated in every cycle, however, no pregnancy was observed, as indicated by the animal having a menstrual period at or before the expected time therefor. While the results tabulated demonstrate the efficacy of the entire procedure, it was observed for the particular structure utilized in the primary immunization, i.e. Structure (I), antibody cross reactivity with LH was observed. Such cross reactivity may be avoided by the utilization of the fragment conjugation procedures set forth in detail hereinabove.

EXAMPLE XXV

Figure 3:
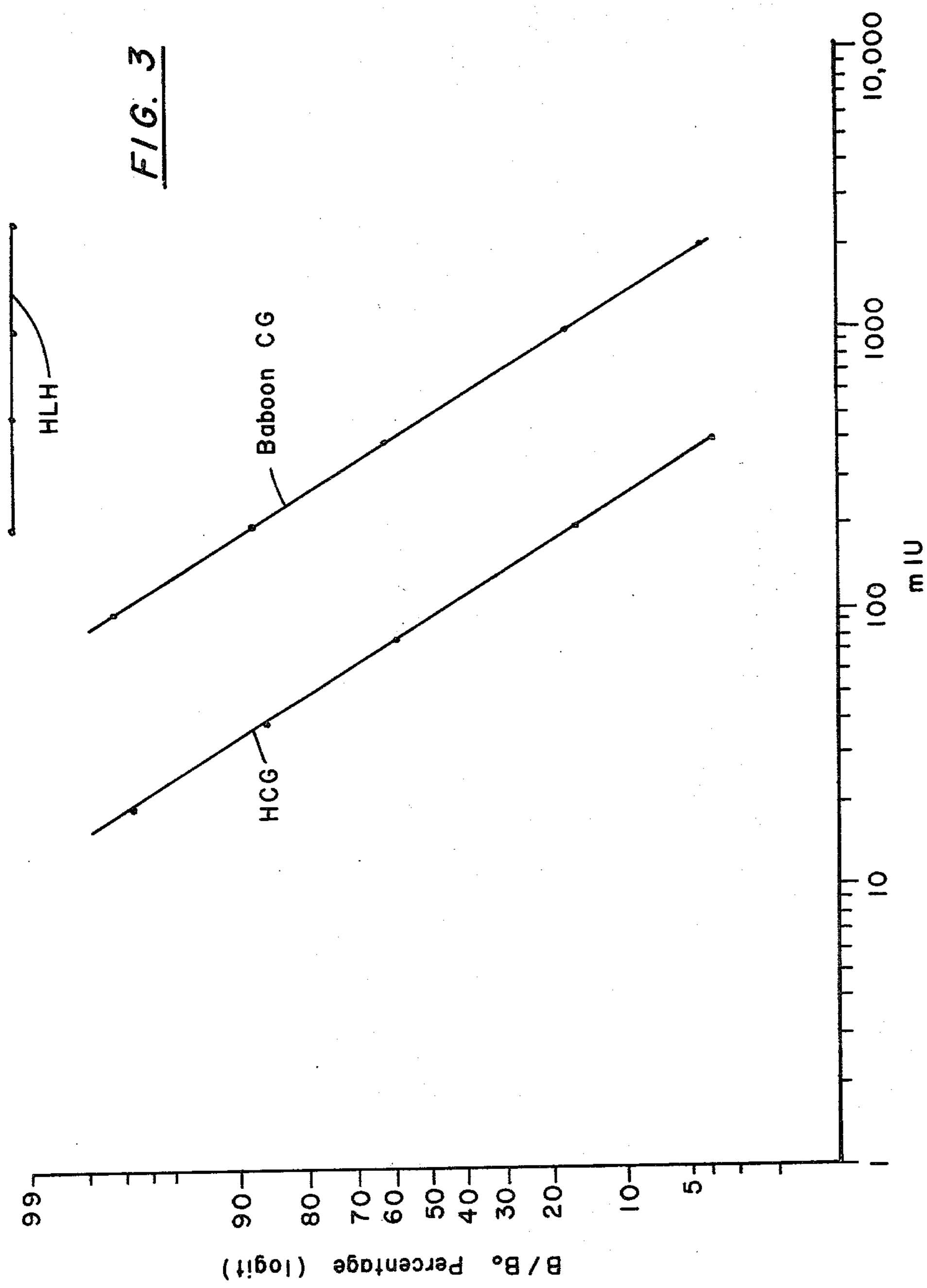
FIG. 3 shows three dose response lines illustrating the specificity of antibody response to a CG antigen formulated in accordance with the invention.

The specificity of antibody response to a CG fragmentmacromolecular carrier is represented by the instant experiment. A 35 amino acid sequence [Structure (II), herein "synthetic peptide"] of the HCG beta subunit was conjugated with bovine gamma-globulin and administered to a baboon. Varying doses of each of these three hormones were tested for their ability to compete with $I^{125}$-labeled synthetic peptide [Structure (II)] bound to the antiserum. The results are set forth in FIG. 3. Note from the figure that Human LH was ineffective for displacement of tracer antigen at doses up to 2.5 IU (international units). Since HCG displaced antigen at a dose of 20 mIU, the cross-reactivity with HLH in this assay system was less than 0.8%. Baboon CG also displaced $I^{125}$-labeled antigen in this assay and, based on biological potency of the two hormones, was about 20% as effective as HCG.

EXAMPLE XXVI

The following experiments were carried out to determine whether the carbohydrate chains contained in the C-terminal 37 residues of β-HCG influence the immunogenicity of that peptide.

TABLE 2

| Breeding of Immunized Baboons [Diazo-β-HCG presensitized] Booster: Diazo-β-hCG-(111-145) | | | | | |
|---|---|---|---|---|---|
| 1 | | | 2 | | |
| Pre-Mate Titer | Ovul. | Preg. | Pre-Mate Titer | Ovul. | Preg. |
| Mating No. 1 | | | | | |
| 5.00 | + | − | 4.20 | + | − |
| Mating No. 2 | | | | | |
| 4.25 | + | − | 4.10 | + | − |
| Mating No. 3 | | | | | |
| 4.22 | + | − | 4.00 | + | − |
| Mating No. 4 | | | | | |
| 4.17 | + | − | 3.89 | + | − |
| Mating No. 5 | | | | | |
| 3.80 | + | − | 3.76 | + | − |
| Mating No. 6 | | | | | |
| 6.65 | + | − | 5.00 | + | − |
| Mating No. 7 | | | | | |
| 5.90 | + | − | 4.75 | + | − |
| Mating No. 8 | | | | | |
| 5.10 | + | − | 4.20 | + | − |
| Mating No. 9 | | | | | |
| 5.00 | + | − | 4.25 | + | − |
| Mating No. 10 | | | | | |
| 4.66 | + | − | 4.00 | + | − |

A peptide representing amino acid residues 109-145 of β-HCG was isolated from a chymotryptic digest of reduced and carboxymethylated β-HCG by procedures reported by Keutmann, H. T.; Williams, R. M., J. Biol. Chem. 252, 5393-5397 (1977). This peptide is identified in Table 3 as P-1. The purity of the peptide was confirmed by amino acid and terminal end group analyses. A portion of the isolated peptide was treated with anhydrous hydrofluoric acid (HF) to remove carbohydrate moieties and repurified by column chromatography according to methods described by Sakakibara S. et al, Bull. Chem. Soc. Japan, 40, 2164-2167 (1967). This portion of the isolated peptide is identified in Table 3 as P-2. Complete removal of the sugar chains were confirmed by carbohydrate analysis; See Nelson, Norton, J. Biol. Chem. 153, 375-380 (1944). A third peptide with the amino acid sequence 109-145 of β-HCG was prepared synthetically using the solid state synthesis procedure of Tregear, G. W. et al., Biochem. 16, 2817 (1977). This third peptide is identified in Table 3 as P-3. Highly purified HCG was used in all immunological experiments where reference was made to intact HCG.

Preparation of Immunogens and Immunizations

Conjugates of the three peptides were prepared to keyhole-limpet hemocyanin (KLH) using tolulene diisocyanate. A peptide-carrier ratio of 4-6 peptides per 100,000 daltons of carrier was obtained for different conjugates prepared according to amino acid analyses. Rabbits were immunized with conjugates by three multiple site intramuscular injections of 1.0 mg. of conjugate in 0.5 ml. of saline emulsified with an equal volume of Freund's complete adjuvant. Injections were given at 3 weeks intervals and weekly blood samples were collected from 3-20 weeks of immunization.

Evaluation of Antisera

Antisera to all conjugates were monitored for antibody levels by reacting dilutions of sera with $I^{125}$ labeled HCG (chloramine T method) at 4° C. for 5 days and precipitating immune complexes with sheep anti-rabbit gamma globulin serum. Antibody levels were determined by assessing dilution curves in which a linear correlation between dilution and binding of labelled antigen at equilibrium occurred. At least 3 points in each curve were used in calculating levels. These levels were expressed as μg. HCG bound per ml. of undiluted serum calculated by multiplying mass of labelled antigen bound by serum dilution.

A radioimmunoassay system employing $I^{125}$ HCG and antisera raised to peptide conjugates was used to determine the relative ability of HCG and peptides to compete with labeled HCG. Peak antibody levels from each rabbit were evaluated in these studies. Antigens and antisera contained in phosphate-buffered saline (pH 7.4) BSA (1%) were added to test tubes and incubated at 4° for 5 days. Separation of free and bound tracer HCG was accomplished by the addition of sheep anti-rabbit gamma globulin serum and further incubated for 48 hours followed by centrifugation. Assessment of parallelism of dose response curves was accomplished using methods described by Rodbard, D. in: Odell, W. D. and Daughaday, W. H., eds., "Competitive Protein Binding Assays," J. B. Lippincott, Phila. Pa. (1971). The ability of unlabelled HCG and peptides to compete with $I^{125}$ HCG for antibody binding sites was expressed as moles of unlabeled antigen, per mole of unlabeled HCG, required to reduce the binding of labeled HCG by 50%. For this purpose molecular weights for HCG, P-1, P-2, and P-3 of 38,000, 7,000, 3,990, and 3,990 respectively were used. The molecular weight of the P-1 peptide was an estimate since the contribution of the 4 carbohydrate chains to its size was not determined. Four radioimmunoassays were performed with each of the 11 antisera studied and the results presented as the mean of the four values.

RESULTS

Parallel dose response curves of HCG and peptides were observed in all radioimmunoassays. In the assay system employed, 200–400 moles of unlabeled HCG was required per mole of labeled HCG at 50% binding of the latter to antisera. There was no detectable difference among antisera to the 3 peptide conjugates in the ability of intact HCG to compete with labeled hormone for antibody binding sites.

Data obtained from comparing the ability of HCG and peptides to compete with $I^{125}$ HCG for binding to anti-peptide sera revealed some qualitative differences in the antisera (Table 2). Much larger quantities of P-2 peptide and P-3 peptide were required to reduce $I^{125}$ HCG binding than was required by P-1 peptide when sera against the P-1 peptide was tested. While similar quantities of P-2 and P-3 peptides were required to inhibit one mole of labeled HCG binding, these were 2–10 times the amounts required by the P-1 peptide.

Differences in the quantities of peptides required to compete with an equivalent mass of labeled HCG were less using antisera raised to carbohydrate-free natural peptide (P-2). More P-1 peptide was needed for an equal reduction in binding than the other 2 peptides. No significant difference could be detected in the quantities of P-2 or P-3 peptides required among the 3 antisera tested.

Approximately 1.5–2.0 times as much P-1 peptide was required to compete equally with $I^{125}$ HCG for antibodies raised to the P-3 peptide but P-2 peptide reacted nearly as well as did the synthetic peptide.

DISCUSSION

Despite low levels of antibodies obtained in this study, the carbohydrate-containing peptide was not more immunogenic than those without this moiety when conjugates to both were prepared in the same manner

TABLE 3

Mean Quantities of HCG and 109-145 C-Terminal β-HCG Peptides Required to Compete with $I^{125}$HCG at 50% Binding of Labelled Hormone

| | Unlabelled Antigens | | | |
|---|---|---|---|---|
| Antisera Rabbit No. | HCG mol/mol HCG $I^{125}$ (X ± SE) | P-1 mol/mol HCG $I^{125}$ (X ± SE) | P-2 mol/mol HCG $I^{125}$ (X ± SE) | P-3 mol/mol HCG $I^{125}$ (X ± SE) |
| Anti P-1 | | | | |
| 78 | 284 (12.6) | 430 (11.8) | 4565 (200.8) | 3628 (154.1) |
| 79 | 350 (13.5) | 404 (18.5) | 855 (33.4) | 881 (42.2) |
| 171 | 403 (17.7) | 343 (9.9) | 899 (35.1) | 759 (37.1) |
| 173 | 377 (16.5) | 320 (13.9) | 1448 (72.4) | 1536 (73.7) |
| Anti P-2 | | | | |
| 93 | 247 (11.8) | 385 (18.2) | 264 (12.5) | 268 (12.73) |
| 94 | 294 (14.1) | 431 (15.5) | 362 (15.2) | 329 (13.8) |
| 252 | 201 (9.6) | 296 (12.4) | 216 (7.7) | 205 (9.0) |
| Anti P-3 | | | | |
| 405 | 496 (23.6) | 998 (47.4) | 628 (27.6) | 309 (13.6) |
| 411 | 489 (20.5) | 1200 (50.4) | 678 (29.7) | 413 (16.1) |
| 416 | 364 (13.1) | 581 (20.9) | 400 (14.4) | 271 (12.8) |
| 417 | 340 (14.9) | 474 (18.4) | 176 (6.8) | 105 (4.6) |

From these studies, it can be concluded that although antibodies to carbohydrate free peptides are qualitatively different than those to the natural peptide, antisera generated to the synthetic peptide reacted with HCG as well as antisera to natural peptides and equivalent to natural and synthetic peptides elicited similar anti-HCG levels in rabbits.

EXAMPLE XXVII

In this Example, a polypeptide fragment structure having an —SH group is activated utilizing the following reagent:

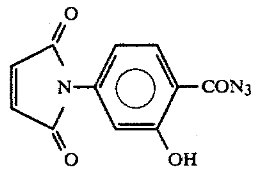

A solution of the reagent (1.2 eq. per —SH group in the polypeptide) in a suitable water miscible organic solvent, such as dioxane, is added to a solution of the polypeptide fragment structure, e.g. Structure (XII) (which has had its amino groups blocked) in aqueous buffer at pH 6.5. After 2 hours, the solvent is removed at a temperature of less than 30° C. under vacuum, and to the residue are added water and ethyl ether (1:1). The aqueous layer is separated and its pH adjusted to approximately 8.5 by the addition of sodium hydroxide solution and this alkaline mixture is added rapidly to an aqueous solution of the carrier, e.g. the above described influenza subunit, maintained at pH 8.5 by a suitable buffer. After a further 4 hours, the conjugate is isolated, by gel filtration.

EXAMPLE XXVIII

With the following reagent:

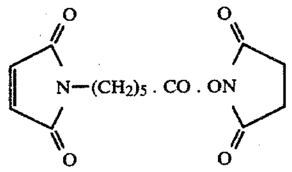

a solution or suspension of a carrier containing no sulfhydryl groups such as Flagellin in a suitable aqueous buffer at a pH 6.5 is treated with the required (1.2 eq/-$NH_2$ desired to be reacted) amount of a solution of the reagent in dimethylformamide. After 1 hour, the modified carrier is isolated by column chromatography and added to buffer at pH 6–7. This is then treated with a solution of the selected fragment (containing sulfhydryl groups) in the same buffer and the reaction is allowed to proceed for 12 hours before the conjugate is isolated by column chromatography.

EXAMPLE XXIX

Modification of non-sulfhydryl containing peptide fragments [e.g. Structure (II)] or a carrier such as Flagellin to a sulfhydryl containing one via "thiolactonization" is carried out as follows:

The peptide is dissolved in a 1 M aqueous solution of imidazole containing 0.5% of ethylenediamine tetraacetic acid at a pH of 9.3 under an atmosphere of nitrogen and a 100 fold excess of N-acetylhomocysteine thiolactone is added in three portions at eight hour intervals. After a total of 30 hours, the pH is adjusted to 3–4 with acetic acid and the modified peptide is isolated by gel chromatography and elution with 0.5 M acetic acid.

EXAMPLE XXX

The carrier protein is reacted with the N-hydroxysuccinimide ester of a halo-(either chloro, bromo or iodo) acetic acid in the general procedure described in the first part of Example XXVIII thus yielding a modified carrier containing the required number of halomethyl alkylating groups as desired.

To a solution of the sulfhydryl containing peptide [e.g. Structure (XII)] in a phosphate buffer at pH 6.5–7.0 under nitrogen at room temperature is added an aqueous solution or suspension of the modified carrier prepared above. The mixture is stirred for 12 hours. It is then washed with ethyl acetate and the conjugate contained in the aqueous phase is purified by dialysis, gel chromatography and lyophilization.

Should neither the carrier nor polypeptide fragment contain a sulfhydryl group, one may be introduced into either of them by the standard procedures such as "thiolactonization" described above under Example XXIX.

What is claimed is:

1. A modified polypeptide for isoimmuniogically controlling biological action in a mammal by antibody formation, consisting of a protein hormone, a non-hormonal protein, or a fragment of either which has been chemically modified outside the body of said mammal, said protein hormone, non-hormonal protein or fragment having the properties of:

(a) in unmodified form, being non-immunogenic to said mammal and having a moleculr structure similar to an endogenous protein hormone or a non-hormonal protein, the biological function of which it is desired to inhibit, or fragment of either and (b) in modified form, causing antibodies to be formed in the body of the mammal which inhibit the biological function of said endogenous protein hormone or non-hormonal protein following administration of the modified form into the body of said mammal.

2. A modified polypeptide according to claim 1 to which there has been chemically added 1–40 modifying groups per protein hormone, non-hormnal protein, or fragment thereof.

3. A modified polypeptide according to claim 1 to which there has been chemically added 5–30 modifying groups per protein hormone, non-hormonal protein, or fragment thereof.

4. A modified polypeptide according to claim 1 to which there has been chemically added 10–26 modifying groups per protein hormone, non-hormonal protein, or fragment thereof.

5. A modified polypeptide according to claim 1 wherein said polypeptide is a natural protein reproductive hormone.

6. A modified polypeptide according to claim 1 wherein said polypeptide is FSH, HCG, LH, HPL, or prolactin.

7. A modified polypeptide according to claim 1 wherein said polypeptide is gastrin, angiotension II, growth hormone, or somatomedian.

8. A modified polypeptide according to claim 1 wherein said polypeptide is HCG, FSH, or a beta subunit thereof.

9. A modified polypeptide according to claim 3 wherein said polypeptide is the beta subunit of HCG.

10. A modified polypeptide according to claim 4 wherein said polypeptide is the beta subunit of HCG.

11. A modified polypeptide according to claim 2 wherein said polypeptide is the beta subunit of FSH.

12. A modified polypeptide according to claim 1 wherein said polypeptide is of the chemical configuration:

Asp-His-Pro-Leu-Thr-Aba-Asp-Asp-Pro-Arg-Phe-Gln-Asp-Ser-Ser-Ser-Ser-Ser-Lys-Als-Pro-Pro-Pro-Ser-Leu-Pro-Ser-Pro-Ser-Arg-Leu-Pro-Gly-Pro-Ser-Asp-Thr-Pro-Ile-Leu-Pro-Gln-Pro-Pro-Pro-Pro-Pro-Pro-Cys;

Asp-Asp-Pro-Arg-Phe-Gln-Asp-Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln-Pro-Pro-Pro-Pro-Pro-Pro-Cys;

Asp-Asp-Pro-Arg-Phe-Gln-Asp-Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln-Cys;

Thr-Cys-Asp-Asp-Pro-Arg-Phe-Gln-Asp-Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln;

Asp-His-Pro-Leu-Thr-Aba-Asp-Asp-Pro-Arg-Phe-Gln-Asp-Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln-Cys; or

Cys-Pro-Pro-Pro-Pro-Pro-Pro-Asp-Asp-Pro-Arg-Phe-Gln-Asp-Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln.

13. A modified polypeptide according to claim 1 wherein said polypeptide is of the chemical configuration:

Asp-Asp-Pro-Arg-Phe-Gln-Asp-Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln;

Gln-Aso-Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln;

Cys-Pro-Pro-Pro-Pro-Pro-Pro-Ser-Asp-Thr-Pro-Ile-Leu-Pro-Gln, Asp-Asp-Pro-Arg-Phe-Gln-Asp-Ser-Pro-Pro-Pro-Pro-Pro-Pro-Cys;

Phe-Gln-Asp-Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln;

Asp-Asp-Pro-Arg-Phe-Gln-Asp-Ser-Ser-Ser-Ser-Lys-Als-Pro-Pro-Pro-Ser-Leu-Pro-Ser;

Asp-Asp-Pro-Arg-Phe-Gln-Asp-Ser-Pro-Pro-Pro-Cys-Pro-Pro-Pro-Ser-Asp-Thr-Pro-Ile-Leu-Pro-Gln; or

Asp-Asp-Pro-Arg-Phe-Gln-Asp-Ser-Pro-Pro-Pro-Pro-Pro-Pro-Cys-Pro-Pro-Pro-Pro-Pro-Pro-Ser-Asp-Thr-Pro-Ile-Leu-Pro-Gln.

14. A modified polypeptide according to claim 1 wherein said polypeptide comprises an 8–41 amino acid chain consisting of the C-terminal residues of an HCG beta subunit.

15. A modified polypeptide according to claim 1 wherein said polypeptide comprises a 20–44 amino acid chain consisting of the C-terminal residues of an HCG beta subunit.

16. A modified polypeptide according to claim 1 wherein said polypeptide is modified by addition of at least one of a diazosulfanilic acid, dinitrophenol, trinitrophenol, S-acetomercaptosuccinic anhydride, (poly)-tyrosine, (poly)alanine, (poly)dextran, thyroglobulin, or a combination thereof.

17. A modified polypeptide according to claim 1 wherein said polypeptide is modified by addition of a (poly)tryosine, (poly)alanine or a mixture thereof.

18. A modified polypeptide according to claim 1 wherein said polypeptide is modified by addition of a diazosulfanilic acid.

19. A modified polypeptide according to claim 6 wherein said polypeptide is modified by addition of at least one of a diazosulfanilic acid, dinitrophenol, trinitrophenol, S-acetomercaptosuccinic anhydride, (poly)-tyrosine, (poly)analine, (poly)dextran, thryoglobulin, or a mixture thereof.

20. A modified polypeptide according to claim 7 wherein said polypeptide is modified by addition of at least one of a diazosulfanilic acid, dinitrophenol, trinitrophenol, S-acetomercaptosuccinic anhydride, (poly)-tyrosine, (poly)alanine, (poly)dextran, thryoglobulin, or a mixture thereof.

21. A modified polypeptide according to claim 8 wherein said polypeptide is modified by addition of a diazosulfanilic acid.

22. A modified polypeptide according to claim 10 wherein said polypeptide is modified by addition of a diazosulfanilic acid.

23. A modified polypeptide according to claim 11 wherein said polypeptide is modified by addition of a diazosulfanilic acid.

24. A modified polypeptide according to claim 12 wherein said polypeptide is modified by addition of a diazosulfanilic acid.

25. A modified polypeptide according to claim 1 wherein said polypeptide is modified by addition of diazosulfanilic acid, dinitrophenol, trinitrophenol, S-acetomercaptosuccinic anhydride, (poly)tyrosine, (poly)alanine, (poly)dextran, thyroglobulin, biodegradable polydextran, natural proteins, polymerized sugars, serum protein, a virus or a mixture thereof.

26. A modified polypeptide according to claim 1 wherein said polypeptide is modified by addition of sucrose copolymerized with epichlorohydrin.

27. A modified polypeptide according to claim 8 wherein said polypeptide is modified by addition of diazosulfanilic acid dinitrophenol, trinitrophenol, S-acetomercaptosuccinic anhydride, (poly)tyrosine, (poly)alanine, (poly)dextran, thyroglobulin, biodegradable polydextran, natural proteins, polymerized sugar, serum protein, a virus or a mixture thereof.

28. A modified polypeptide according to claim 8 wherein said polypeptide is modified by addition of sucrose copolymerized with epichlorohydrin.

29. A modified polypeptide according to claim 12 wherein said polypeptide is modified by addition of diazosulfanilic acid, dinitrophenol, trinitrophenol, S-acetomercaptosuccinic anhydride, (poly)tyrosine, (poly)alanine, (poly)dextran, thyroglobulin, biodegradable polydextran, natural proteins, polymerized sugar, serum protein, a virus or a mixture thereof.

30. A modified polypeptide according to claim 13 wherein said polypeptide is modified by addition of diazosulfanilic acid, dinitrophenol, trinitrophenol, S-acetomercaptosuccinic anhydride, (poly)tyrosine, (poly)alanine, (poly)dextran, thyroglobulin, biodegradable polydextran, natural proteins, polymerized sugars, serum protein, a vuris or a mixture thereof.

31. A modified polypeptide according to claim 25 wherein said virus is diphtheria virus.

32. A modified polypeptide according to claim 6 wherein said polypeptide is modified by addition of diphtheria toxoid.

33. A modified polypeptide according to claim 1 wherein said polypeptide is HCG or a sub-unit thereof.

34. A modified polypeptide according to claim 33 wherein said sub-unit is Thr-Cys-Asp-Asp-Pro-Arg-Phe-Gln-Asp-Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln.

35. A modified polypeptide according to claim 33 or 34 wherein said polypeptide is modified by addition of diptheria toxoid.

* * * * *